United States Patent [19]

Greenquist et al.

[11] Patent Number: 4,668,619

[45] Date of Patent: * May 26, 1987

[54] MULTILAYER HOMOGENEOUS SPECIFIC BINDING ASSAY DEVICE

[75] Inventors: Alfred C. Greenquist; Thomas M. Li; Patricia A. Rupchock; Richard J. Tyhach, all of Elkhart; Bert Walter, South Bend, all of Ind.

[73] Assignee: Miles Laboratories, Inc., Elkhart, Ind.

[*] Notice: The portion of the term of this patent subsequent to Dec. 14, 1999 has been disclaimed.

[21] Appl. No.: 632,946

[22] Filed: Jul. 20, 1984

Related U.S. Application Data

[63] Continuation of Ser. No. 381,218, May 24, 1982, abandoned, which is a continuation of Ser. No. 202,378, Oct. 30, 1980, abandoned.

[51] Int. Cl.$^4$ ............... G01N 33/543; G01N 33/545; G01N 33/566
[52] U.S. Cl. ......................... 435/7; 435/805; 436/501; 436/518; 436/531; 436/535; 436/810; 436/817; 422/56; 422/57
[58] Field of Search ............... 436/501, 502, 518, 531, 436/535, 810, 817; 422/56, 57, 61; 435/7, 805

[56] References Cited

U.S. PATENT DOCUMENTS

| | | | |
|---|---|---|---|
| 3,641,235 | 2/1972 | Weiss | 424/8 |
| 3,802,842 | 4/1974 | Lange et al. | 435/805 |
| 4,016,043 | 4/1977 | Schuurs et al. | 195/103.5 |
| 4,363,874 | 12/1982 | Greenquist | 435/805 |
| 4,442,204 | 4/1984 | Greenquist | 435/805 |
| 4,447,529 | 5/1984 | Greenquist et al. | 435/805 |
| 4,461,829 | 7/1984 | Greenquist | 435/805 |

FOREIGN PATENT DOCUMENTS 2241646 6/1972 Fed. Rep. of Germany.
2537275 4/1975 Fed. Rep. of Germany.

*Primary Examiner*—Esther M. Kepplinger
*Attorney, Agent, or Firm*—Andrew L. Klawitter

[57] ABSTRACT

A homogeneous specific binding assay device, a method for its preparation, and a method for its use in determining a ligand, such as antigen, hapten, or antibody, in, or the ligand binding capacity of, a liquid sample. The test device comprises a solid carrier member, such as a fibrous web matrix, e.g., paper, or a polymeric film or gel, incorporated with reagents for a homogeneous specific binding assay system which produces a detectable response, usually an electromagnetic radiation signal, that is a function of the presence or amount of the ligand in or the ligand binding capacity of the sample. Useful homogeneous specific binding assay systems include those involving enzyme substrate labels, enzyme prosthetic group labels, and enzyme labels. The detectable response preferably is a luminescent, fluorescent, spectrophotometric, or colorimetric response, which is measurable by visual observation or instrument means.

6 Claims, 16 Drawing Figures

MULTILAYER HOMOGENEOUS SPECIFIC BINDING ASSAY DEVICE

This is a continuation of application Ser. No. 381,218, filed May 24, 1982, now abandoned, which is a continuation of application Ser. No. 202,378, filed 10/30/80, abandoned.

BACKGROUND OF THE INVENTION

1. Field of the Invention

This invention relates to test devices and methods for their use in determining a ligand in or the ligand binding capacity of a liquid sample based on a specific binding assay, e.g., immunoassay, principle. In particular, this invention relates to solid state carrier elements incorporated with homogeneous specific binding assay reagents.

Test devices in the form of test strips and similar solid state analytical elements have become commonplace in the analysis of various types of samples, particularly liquid samples in the nature of biological fluids, industrial fluids, and so forth, because of the convenience and speed afforded by their use. Test strips designed for detecting various clinically significant substances in biological fluids, such as serum and urine, in particular have been found to be very advantageous in assisting the diagnosis and treatment of disease states in man and animals.

Conventional test devices of the test strip type generally comprise a carrier member such as an absorbent or bibulous matrix, e.g., paper, incorporated with reagents which interact with the constituent or constituents of a liquid sample under assay to provide a detectable response, usually an electomagnetic radiation signal such as a color change. The sample under assay is contacted with the reagent incorporated carrier member, such as by momentarily immersing the device in the sample or by applying an aliquot of the sample to the element, and the response is observed or measured after a set period of reaction time. The great advantage of such test devices is the convenience of their routine use, not requiring the time or skills of a technician for reagent additions to the sample and providing a readily observable or instrument readable signal. Moreover, a readily observable or instrument readable signal is rapidly provided.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such conventional test strips interact with the constituent or constituents to be determined by direct chemical reaction and, for this and other reasons, have limited sensitivity, being applied to the detection of substances that are present in liquid samples at concentrations in the millimolar range or above.

On the other hand, the development of specific binding assay techniques has provided extremely useful analytical methods for determining various organic substances of diagnostic, medical, environmental and industrial importance which appear in liquid mediums at very low concentrations. Specific binding assays are based on the specific interaction between the ligand, i.e., the bindable analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with reagent means of various compositions. Such compositions include a labeled conjugate comprising a binding component incorporated with a label. The binding component in the labeled conjugate participates with other constituents, if any, of the reagent means and the ligand in the medium under assay to form a binding reaction system producing two species or forms of the labeled conjugate; a bound-species and a free-species. In the bound-species the binding component, e.g., a hapten or antigen, in the labeled conjugate is bound by a corresponding binding partner, e.g., an antibody, whereas in the free-species, the binding component is not so bound. The relative amount or proportion of the labeled conjugate that results in the bound-species compared to the free-species is a function of the presence (or amount) of the ligand to be detected in the test sample.

Where the labeled conjugate in the bound-species is essentially indistinguishable in the presence of the labeled conjugate in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, the separation step can be avoided, and the assay is said to be "homogeneous".

The first discovered type of highly sensitive specific binding assay was the radioimmunoassay which employs a radioactive isotope as the label. Such an assay necessarily must follow the heterogeneous format since the monitorable character of the label is qualitatively unchanged in the free- and bound-species. Because of the inconvenience and difficulty of handling radioactive materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, such as chemiluminescence, fluorescence emission, or color change, related to the presence or amount of the ligand under assay in the liquid sample.

Commercially available test means for performing specific binding assays are usually in the form of test kits comprising a packaged combination of containers holding solutions or rehydratable compositions of the reagents necessary for carrying out the assay. To perform the actual assay method, aliquots of such solutions must be manually or instrumentally dispensed into a reaction vessel with the sample. If manually dispensed, the assay consequently requires the time and skill of a technician, and if instrumentally dispensed, the assay consequently requires the expense and maintenance of dispensing apparatus.

2. Brief Description of the Prior Art

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Patent Spec. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with the remaining reagents of the reaction system, principally the labeled conjugate. After an incubation period, the solid phase device is physically removed from the reaction solution and the label measured either in the solution or on the test device.

Similar devices where the antibody reagent is entrapped in a matrix such as a gel or paper web are described in U.S. Pat. Nos. 3,925,017; 3,970,429; 4,138,474; 3,966,897; 3,981,981 and 3,888,629 and in German OLS No. 2,241,646. Likewise, devices for use in heterogeneous specific binding assays wherein the antibody reagent is fixed to a matrix held in a flow-through column are known (U.S. Pat. Nos. 4,036,947; 4,039,652; 4,059,684; 4,153,675; and 4,166,102). As with all heterogeneous specific binding assay devices, the test device is usually incorporated with less than all of the necessary reagents for carrying out the assay and is merely a means for rendering more convenient the necessary separation step.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay and the low concentrations of ligand or analyte which such devices are intended to determine.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

The prior art lacks a detailed teaching of how to apply homogeneous specific binding assay reagent systems to solid state test devices. British Patent Spec. No. 1,552,607, commonly assigned herewith, describes homogeneous specific binding assay systems employing various novel labels, including chemiluminescent labels, enzyme substrate labels and coenzyme labels. At page 23, lines 12 et seq of this patent there is the suggestion to incorporate the assay reagents with various carriers including liquid-holding vessels or insoluble, porous, and preferably absorbent, matrices such as bibulous papers; polymeric films, membranes, fleeces, or blocks; gels; and the like.

German OLS No. 2,537,275 describes a homogeneous specific binding assay reagent system and poses the possibility of using slides or strips incorporated with antibody in performing the assay. In this suggestion, the labeled conjugate would be first mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element with the labeled conjugate being separately added to the sample under assay prior to contact with the proposed test device.

SUMMARY OF THE INVENTION

The present invention provides a homogeneous specific binding assay test device, a method for its preparation, and a method for its use in determining a ligand in or the ligand binding capacity of a liquid sample. The test device comprises (a) reagents for a homogeneous specific binding assay system which produces a detectable response that is a function of the presence, in a qualitative or quantitative sense, of the ligand in or the ligand binding capacity of the liquid sample under assay, and (b) a solid carrier member incorporated with such reagents. In one embodiment, the carrier member is substantially uniformly incorporated with the assay reagents. The carrier member is preferably a matrix which is absorbent relative to the liquid sample, such as a web matrix composed primarily of natural or synthetic polymer fibers, e.g., paper, or a polymeric film or gel. In another embodiment, the carrier member comprises a multiplicity of zones, for instance, physically distinct layers, each of which zones is incorporated with a different reagent or reagent combination of the assay reagents.

In use, the test device is contacted with the liquid sample, e.g., a biological fluid such as serum or urine, such as by momentarily immersing the reagent incorporated carrier member in the sample or by dispensing an aliquot of the sample onto a surface of the carrier member. The detectable response is thereafter measured, usually after a predetermined incubation or reaction period, either by observation of the technician performing the assay or by instrument means. The detectable response is most commonly an electromagnetic radiation signal, for example, fluorescence, chemiluminescence, color changes and spectrophotometric responses.

Preferred homogeneous specific binding assay systems are those known in the art which involve a label which participates in an enzymatic reaction. One such preferred assay system is that wherein the label is an enzyme prosthetic group and wherein the extent to which an apoenzyme is able to combine with such prosthetic group label to form an active holoenzyme is dependent on the presence of the ligand or binding capacity therefor. The holoenzyme can be measured by its enzymatic activity according to a wide variety of schemes, including colorimetric schemes. Another preferred assay system is that wherein the label is an enzyme substrate and wherein the extent to which an enzyme is able to act on such substrate label to produce a detectable product is dependent on the presence of the ligand or binding capacity therefor. In such a homogeneous specific binding assay system, the detectable product is preferably fluorescent whereby the detectable response from the test device is measurable by a fluorometer. Also useful as the homogeneous specific binding assay system is that wherein the label is an enzyme and wherein the activity of such enzyme label is dependent on the presence of the ligand or binding capacity therefor. In this case also, enzyme activity can be measured in a wide variety of ways.

DESCRIPTION OF THE PREFERRED EMBODIMENTS

Figure 1:
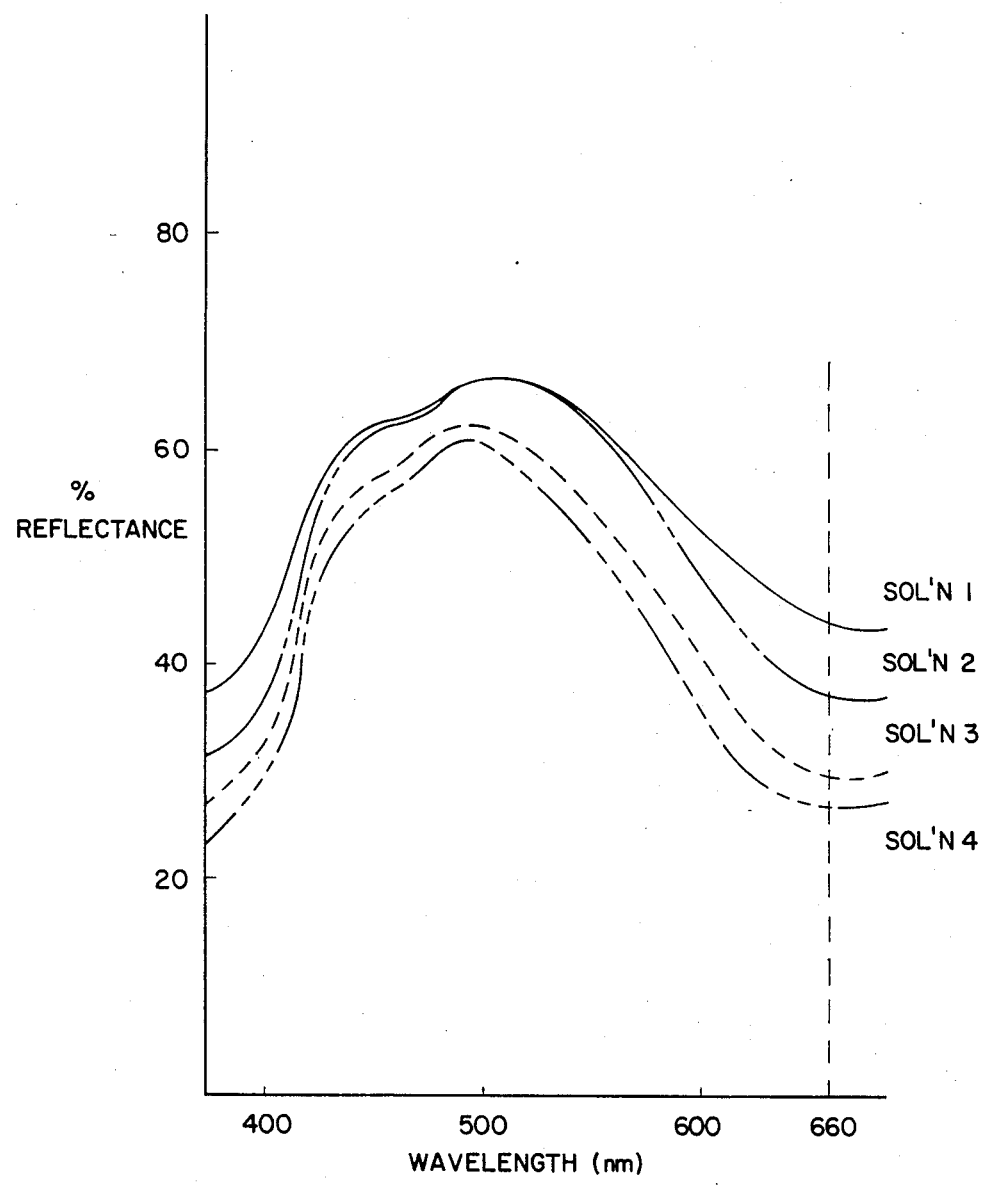
FIGS. 1-16 are graphical representations of data obtained from the experiments described in the examples below.

The present invention provides a test device for use in carrying out homogeneous, nonradioisotopic, specific binding assays, e.g., immunoassays, having all of the convenience features of conventional analytical test strips and other test elements of similar design. As in the case of such conventional devices, the present invention provides a solid carrier, usually a matrix of one sort or another, incorporated with all of the reagents necessary to perform a given assay whereby the user has only the task of bringing the test device into contact with the sample to be tested and measuring the resulting response. Where the entire process is automated, an instrument for performing the same manipulations can have a much simpler design than one having to deal with conventional liquid chemistry systems now used for performing homogeneous specific binding assays.

Homogeneous Specific Binding Assays

Reagents for any homogeneous specific binding assay system may be incorporated in the present test device. In general, homogeneous specific binding assay techniques are based on the special interaction between (1) a conjugate of a binding component and a label and (2) a binding partner to the binding component in the conjugate, whereby a characteristic of the label is different when the labeled conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which interact with the ligand or its binding capacity in the sample in an immunochemical manner. That is, there will be an antigen-antibody or hapten-antibody relationship between reagents and/or the ligand or its binding capacity in the sample. Such assays therefore are termed immunoassays and the special interaction between the labeled conjugate and its binding partner is an immunochemical binding. Thus, in such instances, the binding component of the labeled conjugate is an antigen, hapten or antibody (or a fragment thereof) and the binding partner is its corresponding immunochemical binding partner. However, it is well understood in the art that other binding interactions between the labeled conjugate and the binding partner serve as the basis of homogeneous specific binding assays, including the binding interactions between hormones, vitamins, metabolites, and pharmocological agents, and their respective receptors and binding substances.

Where the sample is being assayed to determine the presence or amount of a particular ligand therein, the reagents for the homogeneous specific binding assay technique comprise, in the usual case, (1) a labeled conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the labeled conjugate. A limiting amount of the binding substance is introduced so that any ligand in the sample will compete with the labeled conjugate for binding to the binding partner. The distribution of the label between the bound-species and the free-species will therefore determine the magnitude of the detectable response from the label, which in turn will be a function of the presence of the ligand. Another scheme for determining a ligand is presented where the labeled conjugate is composed of a labeled binding partner of the ligand and upon binding to the ligand the label is affected in terms of its detectable response. Where ligand binding capacity of the sample is under assay, the labeled conjugate will be composed of the ligand, or a binding analog thereof, chemically coupled to the label whereby the capacity of the sample to bind the labeled conjugate, such as due to the presence of a binding partner of the ligand in the sample, determines the effect made on the detectable signal from the label.

Several different homogeneous specific binding assay systems are known in the art, and the following are examples, without limiting the scope of the present invention, of some such systems contemplated for use in the present test device. The following systems are listed according to the nature of the label used.

1. Enzyme prosthetic group labels

In this system, the label is a prosthetic group of an enzyme, and the ability of a catalytically inactive apoenzyme to combine with the prosthetic group label to form an active enzyme (holoenzyme) is affected by binding of the labeled conjugate with its binding partner. Resulting holoenzyme activity is measurable by conventional detectant systems to yield an ultimate detectable signal. Assay systems of this type are described in commonly assigned, copending application Ser. No. 45,423, filed June 4, 1979 (corresponding to published British Patent Spec. No. 2,023,607). A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In such preferred assay scheme, the FAD-labeled conjugate is preferably of the formula:

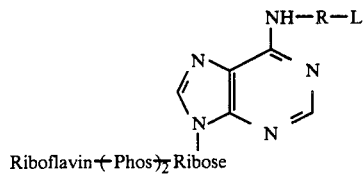

Riboflavin-(Phos)₂-Ribose wherein Riboflavin-(Phos)$_2$-Ribose represents the riboflavin-pyrophosphate-ribose residue in FAD, R is a linking group, and L is the binding component, e.g., the ligand or analog thereof.

2. Enzyme substrate labels

In this system, the label is selected so that the labeled conjugate is a substrate for an enzyme and the ability of the enzyme to act on the substrate-labeled conjugate is affected, either in a positive or negative sense, by binding of the labeled conjugate with its binding partner. Action of the enzyme on the substrate-labeled conjugate produces a product that is distinguishable in some feature, usually a chemical or physical feature such as chemical reactivity in an indicator reaction or such as a photometric character, e.g., fluorescence or light absorption (color). Assay systems of this type are described in commonly assigned, copending applications Ser. Nos. 894,836, filed Apr. 10, 1978 (corresponding to published German OLS No. 2,618,511) and 87,819, filed Oct. 23, 1979; and in *Anal. Chem.* 48: 1933 (1976). *Anal. Biochem.* 77: 55 (1977) and *Clin. Chem.* 23: 1402 (1977). A particularly preferred substrate-labeled assay scheme employs a labeled conjugate of the structure

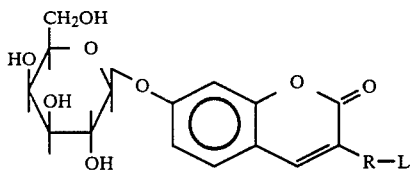

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

3. Coenzyme labels

The labeled conjugate in this system is composed, in its label portion, by a coenzyme-active functionality, and the ability of such coenzyme label to participate in an enzymatic reaction is affected by binding of the labeled conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS No. 2,618,511); and in *Anal. Biochem.* 72: 271 (1976), *Anal. Biochem.* 72: 283 (1976) and *Anal. Biochem.* 76: 95 (1976).

4. Enzyme modulator labels

The labeled conjugate in this system is composed, in its label portion, of an enzyme modulating functionality such as an enzyme inhibitor or stimulator, and the ability of such modulator label to modulate the activity of an enzyme is affected by building of the labeled conjugate with its binding partner. The rate of the resulting enzymatic reaction is measurable by conventional detectant systems to yield an ultimately detectable signal. Assay systems of this type are described in commonly owned U.S. Pat. No. 4,134,792.

5. Enzyme labels

In this system, the label is an enzyme and the activity of the enzyme label is affected by binding of the labeled conjugate with its binding partner. Resulting enzyme activity is measurable by conventional detectant systems to yield an ultimately detectable signal. Assay systems of this type are described in U.S. Pat. Nos. 3,817,837 and 4,043,872.

6. Quenchable fluorescent labels

The labeled conjugate in this system is composed, in its label portion, of a fluorescer whose fluorescence is quenched in some measurable degree when the labeled conjugate is bound by its binding partner, usually a protein such as an antibody. The fluorescent label is measured directly, with its fluorescence being the detectable signal. Assay systems of this type are described in U.S. Pat. No. 4,160,016 and in *J. Clin. Path.* 30: 526 (1977).

7. Fluorescence polarization labels

The label in this system is also a fluorescer; however, the affected characteristic is polarization of fluorescence due to binding of the labeled conjugate by its binding partner, usually a protein such as an antibody. Assay systems of this type are described in *J. Exp. Med.* 122: 1029 (1965).

8. Chemically-excited fluorescent labels

In this system, the label is again a fluorescer, however, the ability of the fluorescer label to be chemically excited to an energy state at which it fluoresces is affected by binding of the labeled conjugate with its binding partner. Chemical excitation of the label is usually accomplished by exposure of the fluorescer label to a high energy compound formed in situ. Assay systems of this type are described in commonly-owned, copending application Ser. No. 4,580, filed Jan. 18, 1979.

9. Double antibody steric hindrance labels

Another assay system is the double antibody immunoassay system described in U.S. Pat. Nos. 3,935,074 and 3,998,943. The labeled conjugate comprises two epitopes, one of which participates in the immunological reaction with the ligand and anti-ligand antibody and the other of which is bindable by a second antibody, with the restriction that the two antibodies are hindered from binding to the labeled conjugate simultaneously. The second epitope can be a fluorescent substance whose fluorescence is quenched by the second antibody binding, or may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Patent Spec. No. 1,560,852.

10. Energy transfer labels

In this system, the label is one member of an energy transfer donor-acceptor pair and the binding partner is conjugated with the other of such pair. Thus, when the labeled conjugate is bound by binding partner, the energy expression of the donor component of the pair is altered by transferance to the acceptor component. Usually, the donor is a fluorescer and the acceptor is a quencher therefor, which quencher may or may not be a fluorescer as well. In such embodiment, the detectable signal is fluorescence, but other detectant systems are possible also. Such assay systems are described in U.S. Pat. Nos. 3,996,345; 4,174,384; and 4,199,559 and in British Patent Spec. No. 2,018,424.

11. Other labels

Other homogeneous specific binding assay systems described in the art which can be used in the present invention include the use of such labels as:

(a) nonenzymic catalysts, such as electron transfer agents (see U.S. Pat. No. 4,160,645);
(b) nonenzymic chemiluminescers (see commonly owned, copending application Ser. No. 894,836 referred to above);
(c) "channeling" labels (see British Patent Spec. No. 2,018,986);
(d) "particle" labels (see British Patent Spec. No. 2,019,562); and
(e) labeled liposome particles (see U.S. Pat. No. 4,193,983).

Ligand

The present assay may be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinnin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferrin, homopexin, fibrinogen, the immunoglobulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetylprocainamide, the amphetamines, the catecholamines, and the antihistamines.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids.

Carrier Member

The carrier member of the present invention can take on a multitude of forms, and is therefore intended as being broad in context. It can be mono- or multi-phasic, comprising one or more appropriate materials or mediums of similar or different absorptive or other physical characteristics. It can be hydrophobic or hydrophilic, bibulous or nonporous. In its most efficient embodiment the carrier member can be carefully tailored to suit the characteristics of the particular homogeneous specific binding assay system to by employed.

Thus, as used herein, the term "carrier member" can comprise any substance, matrix, or surface capable of being incorporated with specific binding assay reagents. It can take on many known forms such as those utilized for chemical and enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Patent, No. 1,349,623, suggests the use of a light-permeable meshwork of thin filaments as a cover for an underlying paper carrier element. This reference also suggests impregnating the paper with part of a reagent system and impregnating the meshwork with other potentially imcompatible chemical or enzymatic reagents. French Patent No. 2,170,397 teaches the use of carrier members having greater than 50% polyamide fibers therein. Another approach to carrier members is disclosed in U.S. Pat. No. 4,046,513 wherein the concept of printing reagents onto a suitable carrier is employed. U.S. Pat. No. 4,046,514 discloses the interweaving or knitting of filaments bearing reagents in a reactant system. All such carrier member concepts can be employed in the present invention, as can others. Preferably the carrier member comprises a bibulous material, such as filter paper, whereby a solution or suspension of the reagents of the specific binding assay system is used to impregnate the carrier member. It can also comprise a system which physically entraps these ingredients, such as in polymeric microcapsules, which then rupture upon contact with the test sample. It can comprise a system wherein the ingredients are homogeneously combined with the carrier member in a fluid or semi-fluid state, which later hardens or sets, thereby entrapping the ingredients.

Whichever material is chosen for the carrier member, whether it be porous to permit incorporation of ingredients such as through saturation with a solution containing them, whether it be nonporous such as for use in printed application of reagents or to support a continuous coating, whether it be woven or knitted, whatever its composition or configuration, it selection will in any event be dictated by anticipated use and by the reagent system. For example, it may be desirable to utilize a multi-step application of reagents. In such a case, two or more solutions or suspensions of reagents are prepared, the carrier member being dipped sequentially into each with drying steps between dippings. In such a case a porous material such as paper might be most advantageous. Alternatively, it might be desirable to utilize a multiphasic carrier member, where two or more layers of porous material are affixed one atop another. Still another approach to carrier member incorporation is to sequentially coat a continuous polymer with coatings containing different reagents of the immunoassay system. Filtering layers can be present in the carrier member to preclude potential interfering agents from reaching the assay system, while permitting access to any analyte present in the sample.

Thus, it can be seen that proper selection of the carrier member is dependent on only two factors: anticipated use and the nature of the specific binding assay system to be employed. Given the present teachings, it becomes a matter of routine experimentation to select the proper carrier member.

Preparation of the Test Device

Also provided is a method of preparing the test device according to the present invention which comprises incorporating a carrier member with the components of the test system. When this incorporation is by impregnation with one or more solutions of the assay reagents according to the invention, the carrier so impregnated is then dried. In addition to impregnation, the devices of the present invention can be made by other suitable techniques such as printing or spraying the composition onto a layer of carrier material or incorporating the solutions into film forming liquids and allowing the combination so prepared to set or solidify.

Where the carrier member comprises multiple layers, e.g., paper or other fibrous material, such layers may be maintained in laminar relationship by adhesives which permit fluid passage between layers. In preparing integral analytical elements using film formers, the layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coating can be accomplished by hand, using a blade coating device, or by machine, using techniques such as dip or bead coating. If machine coating techniques are used, it is often possible to coat adjacent layers simultaneously using hopper coating techniques well known in the preparation of light sensitive photographic films and papers.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions. The lower boiling solvent evaporates more readily and the coating becomes enriched in the liquid which is a poor solvent or nonsolvent. As evaporation proceeds, under proper conditions, the polymer forms as a porous layer. Many different polymers can be used, singly or in combination, for preparing porous blush polymer layers for use in this invention. Typical examples include polycarbonates, polyamides, polyurethanes and cellulose esters such as cellulose acetate. For layers such as those containing a labeled conjugate or other reagent, a coating solution or dispersion including the matrix and incorporated active materials can be prepared, coated as discussed herein and dried to form a dimensionally stable layer.

The thickness of any layer and its degree of permeability are widely variable and depend on actual usage. Dry thicknesses of from about 5 microns to about 100 microns have been convenient, although more widely varying thickness may be preferable in certain circumstances. For example, if comparatively large amounts of interactive material, e.g., polymeric materials like enzymes, are required, it may be desirable to prepare slightly thicker layers.

It can also be desirable to include within a carrier member one or more reflective layers, optionally absorptive to detecting radiation, such as to facilitate signal detection by reflection radiometry, e.g., reflection photometry or a similar technique. Such reflector can be provided by one of the above-described layers or it can be provided by an additional layer that may not have an additional function within the element. Reflective pigments, such as titanium dioxide and barium sulfate, can be used to advantage in a reflecting layer.

Blush polymers can also constitute a suitable reflecting material. In one preferred aspect, blush polymer layers can also incorporate a pigment to enhance reflectivity or other functions. The amount of pigment that can be included in a layer together with a blush polymer is highly variable, and amounts of from about 1 to about 10 parts by weight of pigment per part by weight of blush polymer are preferred, with from about 3 to about 6 parts pigment per part of blush polymer being most preferred.

It can be advantageous to incorporate one or more surfactant materials, such as anionic and nonionic surfactant materials, in the layers of the carrier member. They can, for example, enhance coatability of layer formulations and enhance the extent and range of wetting in layers that are not easily wetted by liquid samples in the absence of an aid such as a surfactant. In layers of the carrier it can also be desirable to include materials that can render nonactive in the analysis of choice, by chemical reaction or otherwise, materials potentially deleterious to such analysis. As mentioned previously herein, the integral analytical elements can be self-supporting or coated on a support. The support can be opaque or transparent to light or other energy. A support of choice for any particular carrier member will be compatible with the intended mode of signal detection. Preferred supports include transparent support materials capable of transmitting electromagnetic radiation of a wavelength within the region between about 200 nm and about 900 nm. The support need not, of course, transmit over the entire 200-900 nm region, although for fluorometric detection of analytical results through the support it is desirable for the support to transmit over a wider band or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

Following are descriptions of some preferred approaches to preparation of the present test device:

Multiple impregnation approach

A layer of carrier material is impregnated with a first solution or suspension of reagents in a first solvent and dried. Thereafter, the carrier material is impregnated with a second solution or suspension of the remaining reagents in a second solvent which prevents interaction with reagents impregnated by the first solvent and dried. In this way, the reagents in the respective solutions are incapable of substantial interaction during preparation of the test device and thus do not react prematurely. In a preferred embodiment, certain first reagents are incorporated with a layer of carrier material using an aqueous dip. A suitable organic solvent is used for the reamining reagents, such as toluene, acetone, chloroform, methylene chloride, n-propanol and ethylene dichloride. This layer is set by allowing the organic solvent to evaporate. Further details are found in the examples which follow.

Multilayer element

A multilayer element is prepared by incorporating a first or overlaying layer with some, but less than all, of the reagents of the specific binding assay system used; incorporating a second or underlaying layer with the remaining reagents; setting, such as by drying, the individual layers; and fixing them into laminar relationship with one another. When absorbent carrier materials are used, these elements are prepared by impregnating individual layers, and drying the layers so impregnated.

The first layer and second layer each have a pair of opposite surfaces. One surface of the first layer is in laminar relationship with one surface of the second layer, sample being applied to the other surface of either of said layers. Reference to a laminar relationship connots the ability of a fluid, whether liquid or gaseous, to pass between superposed surfaces of such layers. Such layers can be contiguous or separated by intervening layers. Any intervening layer should not prevent passage between all layers.

Freeze drying approach

This approach consists of a procedure to incorporate and prevent reaction between incompatible reagents in a single layer analytical element. When using, for example, absorbent carrier materials, a first group of reagents is incorporated with the layer material at elevated temperature (or alternatively by freeze drying) and the treated layer is set. The second group of reagents containing any which will react, under ambient conditions, with the first group, are applied and the element is rapidly frozen. Freezing prevents premature reaction and the subsequent removal of water by freeze drying prevents premature reaction when the layer is brought back to room temperature.

In the preferred embodiment, one group of reagents can be added in aqueous solution to a layer and dried. The addition of a second group of reagents in aqueous solution is followed by rapid freezing and then freeze drying to remove water. This procedure allows the incorporation of and prevents the interaction between some reagents which are only water soluble. In addition, it avoids the use of organic solvents, certain of which may interact deleteriously with some reagents (e.g., enzymes).

The procedure permits formulation of elements utilizing homogeneous specific binding assay reagents in which all reagents are provided within a single layer element.

Reversible complex formation approach

Competition between sample ligand and labeled ligand for binding to a binding partner (here exemplified by an antibody-"Ab") can be summarized by the equation:

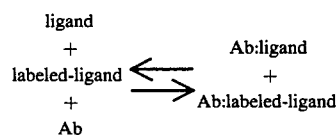

In the system illustrated above, the antibody and the labeled-ligand are kept separate until the introduction of the sample. This embodiment of the described invention makes use of the reverse reaction and reequilibration with the ligand as shown by the equation below:

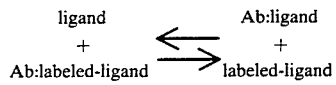

where the amount of displaced labeled ligand is related to the sample ligand concentration. The advantage is that all reagent components can be combined in one incorporation medium to provide a system that requires only the addition of sample to be tested.

Analytical elements are prepared by incubating a given conjugate with its respective antisera for a short period, such as 15 minutes. Then any additional reagents are added and the system allowed to incubate an additional period. The solution so formed is impregnated into or otherwise incorporated with a layer of carrier material which is then allowed to set.

Detectable Response

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The terms "detectable species" and similar terms as used herein, refer to atoms, chemical groups (i.e., a portion of a molecule) or chemical compounds that are themselves directly or indirectly detectable and the term "detectable response", and similar terms as used herein, refer to the detectable manifestation of the presence of such species. Examples are electromagnetic radiation signals such as fluorescence, phosphorescense, chemiluminescence, a change in light absorption, or reflectance in the visible spectrum thereby producing a visible color change, a change in light absorption or reflectance outside the visible range such as the ultraviolet or infrared. As will be apparent to one skilled in the art of immunoassays, the phrase "detectable response", as used herein, is intended in its broadest sense. In addition to electromagnetic radiation signals the term "detectable response" is also meant to include any observable change in a system parameter, such as a change in or appearance of a reactant, observable precipitation of any component in the test sample or a change in any other parameter, whether it be in the immunoassay system or the test sample. Such other detectable responses include electrochemical responses and calorimetric responses. Moreover, the detectable response is one which can be observed through the senses directly or by use of ancillary detection means, such as a spectrophotometer, ultraviolet light-sensing equipment, fluorometer, spectrofluorometer, pH meter and other sensing means. Desirably, such detectability can be conveniently imparted to the full amount of detectable species without affecting the amount of diffusible product resulting from the analyte interactions which are the basis of the intended analysis.

After the analytical result is obtained as a detectable change, it is measured, usually by passing the test element through a zone in which suitable apparatus for reflection, transmission or fluorescence photometry is provided. Such apparatus serves to direct a beam of energy, such as light, through, in one embodiment, the support. The light is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from any residues, such as blood cells or urine sediment, which have been left on or in the layers of the element or from atypical urine colors. Conventional techniques of fluorescence spectrophotometry can also be employed if desired. Furthermore, transmission techniques can be used to detect and quantify the indicating reaction products by reacting a flow of radiant energy, for example, ultraviolet, visible or infrared radiation at one surface of the element and measuring the output of that energy from the opposing surface of the element. Generally, electromagnetic radiation in the range of from about 200 to about 900 nm has been found useful for such measurements, although any radiation to which the element is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

A. PROSTHETIC GROUP-LABELED IMMUNOASSAY TEST DEVICES

EXAMPLE I

A Model System

In order to study various parameters of incorporating the prosthetic group-labeled homogeneous immunoassay reagent system described in Britiish Pat. No. 2,023,607 into a dry test device format, a model system was experimentally devised. The ligand to which the model system was responsive was N-(2,4-dinitrophenyl)-$\epsilon$-aminocaproic acid (hereafter "DNP"). Reagents comprising the immunochemical components of the system included antibody to DNP, a conjugate of DNP and flavin adenine dinucleotide (hereafter "DNP-FAD"), and apoglucose oxidase.

The system was designed to respond to DNP by exhibiting color due to the activation of apoglucose oxidase by the DNP-FAD conjugate. DNP-FAD which does not become bound by antibody is directly proportional to DNP concentration. It is detectable by its ability to combine with apoglucose oxidase to produce active glucose oxidase enzyme. Thus the response system included, in addition to apoenzyme, antibody and conjugate, a glucose oxidase detection system comprising glucose, 3,3',5,5'-tetramethylbenzidine (TMB), and horseradish peroxidase. Upon activation of the apoenzyme to glucose oxidase, a blue color formed due to the oxidation of glucose to hydrogen peroxide and subsequent conversion of TMB to its blue oxidized state in the presence of peroxidase.

1. Preparation of Apoenzyme

Apoenzyme was prepared from a sample of highly purified glucose oxidase obtained from Miles Laboratories, Inc. (Catalog No. 31-619). 10.5 milliliters (ml) of this enzyme solution (1000 units/ml) was mixed in a glass beaker with 4.5 ml of glycerol, and the mixture was cooled to a temperature of 0°–4° C. The pH of the mixture was lowered, using a 10% aqueous solution of sulfuric acid, until a pH of 1.4 was reached. This procedure was carried out with constant stirring with the beaker immersed in an ice bath, and the stirring was continued for 2 hrs. After that time, the solution was poured over a 1.5 by 43 centimeter (cm) column of Sephadex G-50 (medium) cross-linked gel filtration media. The Sephadex had been equilibrated previous to the introduction of the enzyme solution with a 30% by volume aqueous glycerol solution having a pH of 1.4. Following the introduction of the enzyme solution onto the Sephadex column, more of the 30% glycerol solution was used to elute apoenzyme. The effluent was separated into fractions and observed using UV absorbance at 280 nanometers (nm). Those fractions having absorbance at this wavelength were combined with a buffer solution containing 50 milligrams (mg) of activated charcoal and 25 mg of dextran (Pharmacia Company No. T-70). The buffer comprised an aqueous solution which was 1 molar (M) tris-(hydroxymethyl)aminomethane to which glutamic acid was added until a pH of 7.0 was reached. The pH of the resultant effluent solution was then readjusted to 7 using a saturated solution of tris-(hydroxymethyl)aminomethane. This final solution was allowed to stir in an ice bath for 1 hr. The apoenzyme solution was then centrifuged and the supernatant was filtered through 0.5 micrometers ($\mu$m) and 0.22 $\mu$m filters obtained from Millipore Corporation.

2. Preparation of DNP-FAD Conjugate

The conjugate was prepared as follows. $N^6$(Trifluoroacetamidohexyl)adenosine-5'-monophosphate was synthesized by the method Trayer et al., *Biochem. J.*, 139, 609–623 (1974). Fifty-six mg of $N^6$-(trifluoroacetamidohexyl)adenosine-5'-monophosphate [(0.1 millimoles (mmol)] was dissolved in about 10 ml of water, and 25 microliters ($\mu$l) of tri-n-butylamine (0.1 mmol) was added. The water was removed under vacuum, and the residue was dissolved in 10 ml of dry dimethylformamide which was then removed under vacuum. The residue was evaporated from dry dimethylformamide three more times. The final residue was dissolved in 10 ml of dry dimethylformamide. Eighty mg of N,N'carbonyldiimidazole (0.5 mmol) was added and allowed to react for 1.5 hrs. Then 15 $\mu$l water was added and the solvent was removed under vacuum. The residue of $N^6$-(trifluoroacetamidohexyl)adenosine-5'-monophosphate imidazolide was dissolved in 10 ml of dimethylformamide.

Forty-seven milligrams of riboflavin-5'-monophosphate (0.1 mmol), purified by the method of Johnson et al., *Anal. Biochem.*, 86, 526–530 (1978), was dissolved in about 10 ml of water and added dropwise to 20 ml of acetone containing 43 $\mu$l of tri-n-octylamine (0.1 mmol). A precipitate formed before the addition was complete. The solvent was removed with a rotary evaporator until the riboflavin-5'-monophosphate dissolved. Then 5 ml of acetone and 5–10 ml of dimethylformamide were added and the mixture taken to dryness. The residue was dissolved in 15 to 20 ml of dry dimethylformamide and taken to dryness. This procedure was repeated three times. The residue was dissolved in 5 ml dimethylformamide and combined with the above-mentioned 10 ml of solution of the imidazolide in dimethylformamide.

The reaction mixture was allowed to stand at room temperature overnight and then the solvent was removed. The residue was taken up in 50 ml of water and applied to a 2.5×25 cm column of DEAE-cellulose (Whatman DE 23; Whatman, Inc., Clifton, NJ) in the bicarbonate form. The chromatogram was developed with a linear gradient generated with 2 liters of water and 2 liters of 0.3M-ammonium bicarbonate (23 ml fractions were collected). Thin-layer chromatography on silica gel 60 F254 (E. Merck, Darmstadt, West Germany), using ethanol/1M-triethylammonium bicarbonate pH 7.8 (7:3, by volume), showed that fractions numbered 68 to 73 contained major ($R_F$ 0.75) and minor ($R_F$ 0.36) yellow compounds. These fractions were pooled, and the optical adsorption spectrum had maxima at 267 nm, 373 nm, and 450 nm.

The solvent was removed from the pooled material, and the residue was dissolved in about 5 ml of water. This solution was adjusted to pH 11.0 with 5M-NaOH and allowed to stand at room temperature for 9 hrs. Thin-layer chromatography showed that the component with $R_F$ 0.75 disappeared while a new yellow material with $R_F$ 0.37 appeared. The reaction mixture was adjusted to pH 8.0 with hydrochloric acid and applied to a column (2.5×20 cm) of DEAE-cellulose in the bicarbonate form. The chromatogram was developed with a linear gradient of 1 liter of water and 1 liter of 0.2M-ammonium bicarbonate. The yellow effluent from the column was pooled and the solvent was removed. The residue was adsorbed onto 2 g of silica gel which was placed atop a 50 g column of silica gel equilibrated with ethanol/1M-triethylammonium bicarbonate, pH 7.8 (8:2 by volume). The chromatogram was developed with the same solvent, the yellow component with $R_F$ 0.37 was collected, and the solvent was removed. The yield of flavin $N^6$-6-N-aminohexyladenine dinucleotide [hereinafter $N^6$(aminohexyl)FAD] based on absorbance at 450 nm was about 10%.

To 10 ml of 0.21M aqueous sodium bicarbonate containing 0.06 millimoles of $N^6$(aminohexyl)FAD was added dropwise 17 $\mu$l of 2,4-dinitrofluorobenzene (0.13 mmol) in one ml of absolute ethanol with stirring. The reaction mixture was stirred in the dark for four to six hours and then 10 $\mu$l of 2,4-dinitrofluorobenzene (0.08 mmol) dissolved in 0.5 ml of ethanol was added. The reaction mixture was stirred overnight. Thin-layer chromatography on silica gel (silica gel 60, F-254, E. Merck) using an ethanol/triethylammonium bicarbonate, pH 7.5, (7:3) solvent showed that the $N^6$(aminohexyl)FAD had completely reacted.

The reaction mixture was filtered through Whatman #1 paper and the filtrate was applied to a 2.5×56 cm column of Sephadex LH-20 which was equilibrated with 0.3M ammonium bicarbonate. The chromatogram was developed with this solvent and several yellow materials were eluted as separate peaks. The peak eluted between 470 and 590 ml of 0.3M ammonium bicarbonate was the only one which activated apoglucose oxidase. Thin-layer chromatography as described above resolved this material into two yellow fluorescent spots with $R_f$=0.84 and 0.89. The optical absorption spectrum had maxima at 265, 370 and 455 nm.

A sample of the product was allowed to react with a snake venom phosphodiesterase preparation (*Croteus adamatoces*) obtained from Worthington Biochemical Corp. Thin-layer chromatography showed that the reaction products were riboflavin-5'-monophosphate and $N^6$(2,4-dinitrophenyl-aminohexyl)adenosine-5'- monophosphate. It was evident from the intensities of the spots that the one with $R_f=0.84$ was the material being digested by the enzyme. The digestion was not complete after three days.

3. Preparation of Test Device

The device was prepared by incorporating the ingredients into a paper carrier matrix in a two-dip process. The first impregnation dip was an acetone solution made 2 mM in TMB. Pieces of Eaton & Dikeman 205 filter paper measuring 4 cm square were dipped into the TMB solution (first-dip), removed, and dried in a forced air oven at 90° C. for 1–2 minutes.

A second-dip solution was prepared by combining the following ingredients in the order listed:

| Aqueous Buffer (pH 6.4)* | 0.4 ml |
|---|---|
| Glucose (1 M) | 0.2 ml |
| Horseradish Peroxidase (153 units/mg; 1.25 mg/ml) | 0.2 ml |
| Polyvinyl Alcohol (Monsanto 20-30; 10 gm/100 ml water) | 0.2 ml |
| Bovine Serum Albumin (Miles Laboratories, Inc.; 20 mg/ml of water) | 0.05 ml |
| Apoglucose Oxidase (5.0 nanomoles FAD binding sites/ml) | 0.4 ml |
| Partially purified antibody to DNP** | 0.56 ml |

*The Buffer comprises an aqueous solution of 10.8 grams (g) of tris-(hydroxymethyl)aminomethane, 9.7 g glutamic acid and 1.6 g citric acid per 100 ml of solution.
**Partially purified antibody was prepared from a DNP antiserum obtained from Miles Laboratories, Inc. The immunoglobulin fraction was isolated by precipitation with ammonium sulfate as described by Livingston in "Methods in Enzymology", Vol. XXXIV) W. B. Jakoby and M. Wilchek, 3ds.) p. 725, Academic Press (New York, 1974). The final precipitate from this procedure was dissolved in 50 mM potassium phosphate (pH 6.8) to bring the total volume to the original volume of serum used. This solution was dialyzed overnight at 4° C. against 500 volumes of the same buffer (50 mM potassium phosphate).

Prior to use in the present experiment, the apoenzyme solution prepared as above was dialyzed against 20 mM tris-glutamate buffer at a pH of 7.0 and which contained 10% by weight of mannitol.

This second dip solution was then used to impregnate the papers which had previously been impregnated with TMB. The TMB-bearing papers were dipped into the second-dip solution, removed, and dried in a forced air oven at 90° C. for six minutes.

Test devices were prepared having 0.5 cm squares of the dried paper mounted at one end of biaxially oriented polystyrene strips measuring about 0.5×8.3 cm. The mounting was achieved using a double-face adhesive tape available from the 3M Company and known as Double-Stick.

The reagent system was completed by contacting the reagent device as prepared above with aqueous solutions which were made 1 μM in DNP-FAD conjugate. All of the solutions utilized in testing the devices contained that amount of conjugate and either none or varying amounts of the ligand, DNP. Accordingly, four test solutions were made up as follows:

| Test Solution | Contents |
|---|---|
| 1 | 1 μM DNP—FAD |
| 2 | 1 μM DNP—FAD and 1 μM DNP—Caproate |
| 3 | 1 μM DNP—FAD and 4 μM DNP—Caproate |
| 4 | 1 μM DNP—FAD and 10 μM DNP—Caproate |

4. Performance Evaluation

In examining the performance of the test devices, each was wet with 15 μl of one of the above test solutions. After being contacted with the test solution, each device was incubated for 6 minutes in a covered petri dish having a wetted piece of filter paper in the bottom. This served as a humidity chamber.

The performance of the reagent devices prepared and incubated as above-described was analyzed instrumentally using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations. Measurements of the performances of reagents strips in the Rapid Scanner have the following advantages over visual observations of the same devices:

1. The light source and conditions surrounding the sample remains fixed. In visual readings the light source can vary, not only in wavelength components, but also in relation to the locations of the strips being observed.

2. The detector characteristics remain fixed in the Rapid Scanner. In visual observation, the detector (i.e. in the eyes of the observer) varies from person to person and, with the same person, from day to day.

3. The Rapid Scanner allows more precise quantitation of the data than does human observation, thereby permitting comparisons between the results to be made in a more objective manner than with visual observation.

The Rapid Scanner instrument was constructed by the Ames Company Division of Miles Laboratories, Inc., Elkhart, Ind. U.S.A., from whom complete information with respect to structural and performance characteristics are obtainable.

Test devices which had been inoculated with the four solutions were analyzed using the Rapid Scanner. Spectra obtained from this analysis are illustrated in FIG. 1. The four curves of FIG. 1 represent percent reflectance versus wavelength. Of particular interest is the performance of the strips of 660 nm, the maximum absorption wavelength in the blue color range of oxidized TMB. The percent reflectance decreases with increasing ligand concentration, thereby indicating the efficacy of the device in quantitatively analyzing solutions of varying concentrations of DNP-caproate. Moreover, the differences in color with respect to each of the ligand solutions were large enough to enable visual correlation between the color of the test device and the concentration of ligand.

This experiment demonstrates that antibody and apoenzyme can compete simultaneously for the respective conjugate, in this case DNP-FAD, without an ordered sequence of reagent addition. Moreover, it demonstrates the practicality of mixing and storing the reagents of an immunochemical assay system long before the time of actual performance of the assay.

EXAMPLE II

A Unitized Immunoassay Test Device

An experiment was conducted whereby an attempt was made to improve the model system of Example I by incorporating the conjugate directly into the carrier element prior to performing the assay, thereby producing a unitized homogeneous immunoassay test device.

A piece of Buckeye S-22 measuring 3.75 by 6.25 cm was immersed in a first dip solution of 5 mM TMB in acetone containing 0.1 g per 100 ml of an emulsifier (GAF ON-870, General Aniline & Film Corp.). This latter component of the first dip is a polyethylene oxide polymer, the terminal ends of which are capped with a long chain fatty alcohol. The molar ratio of ethylene oxide to fatty alcohol comprising the polymer is 30:1. The paper was then dried at 50° C. for one minute.

Following drying, the paper was immersed in a second-dip solution which was prepared by combining the following ingredients:

| | |
|---|---|
| Aqueous Buffer (1 M tris-glutamate, pH 6.4) | 0.4 ml |
| Glucose (1.0 M) | 0.2 ml |
| Horseradish Peroxidase (153 units/mg, 1.25 mg/ml) | 0.2 ml |
| Polyvinyl Alcohol (Monsanto 20-30; 10 g/100 ml water) | 0.2 ml |
| Bovine Serum Albumin (Miles Laboratories, Inc; 20 mg/ml water) | 0.05 ml |
| Apoglucose Oxidase (50 nanomoles FAD binding sites/ml) | 0.08 ml |
| Partially purified antibody to DNP (See Example I) | 0.27 ml |
| Distilled water | 0.6 ml |

After drying at 50° C. for 12 minutes, the paper was immersed in a third-dip solution prepared by mixing 250 μl of 80 μM DNP-FAD conjugate in water with 9.75 ml n-propanol to yield a dip solution 2 μM in DNP-FAD. Following the third impregnation, the paper was dried at 50° C. for four minutes.

Test devices were prepared having 0.5 cm squares of the triply impregnated paper mounted at one end of biaxially oriented polystyrene strips measuring about 0.5 by 8.3 cm. Mounting was achieved using a double-faced adhesive tape known as Double-Stick (3M Company).

Figure 2:
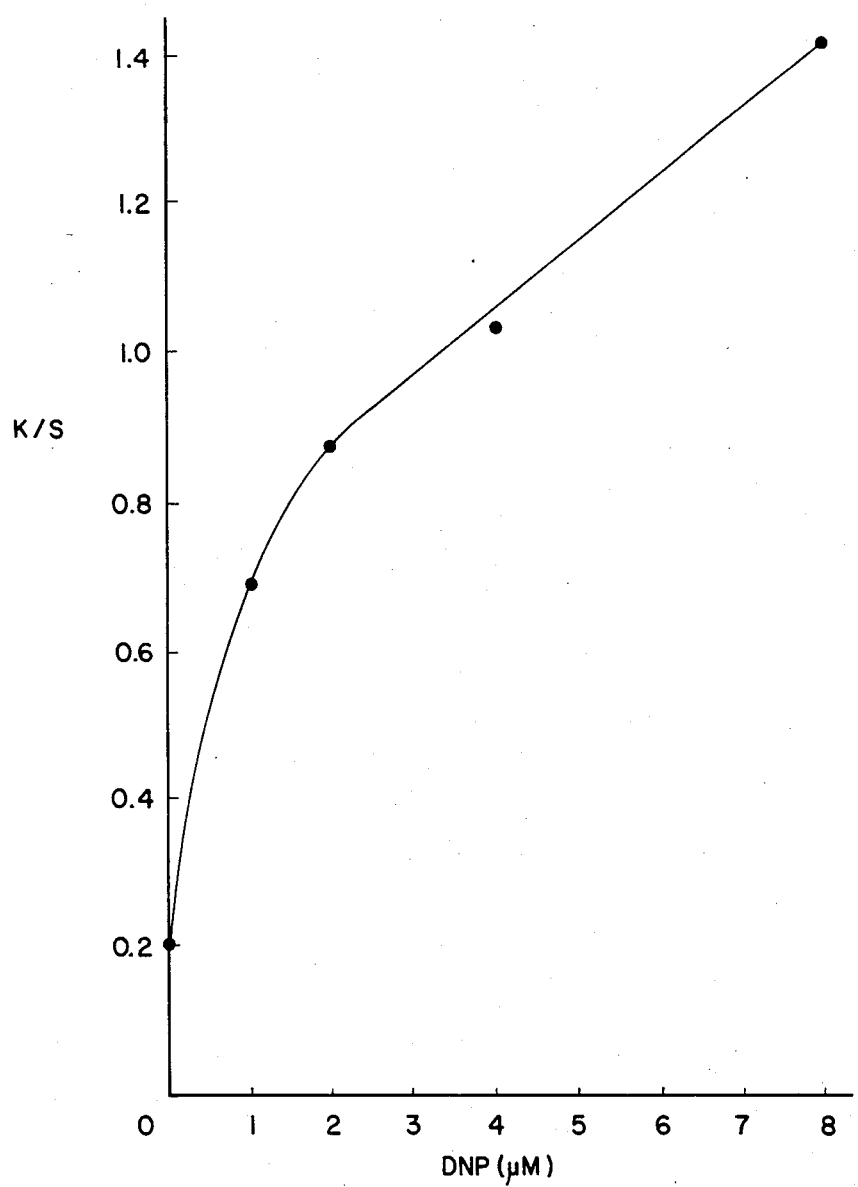

These devices were tested for their responsiveness to various concentrations of DNP by dipping in the respective solutions, incubating the dipped strips for three minutes, and analyzing the strips in the Rapid Scanner (see Example I) to determine reflectance of light. The data obtained at 660 nm is represented graphically in FIG. 2 wherein K/S is plotted against DNP concentration. K/S is defined as follows:

$$\frac{K}{S} = \frac{(1-R)^2}{2R}$$

in which K is a constant, S is the scattering coefficient of the particular reflecting medium, and R is the fraction of reflectance from the test strip. This relationship is a simplified form of the well-know Kubelka-Munk equation (Gustav Kortüm, "Reflectance Spectroscopy", pp. 106-111, Springer-Verlaz, New York (1969)).

The results from the Rapid Scanner were also used to assess performance by calculating color difference units (ΔE) which are presented in Table A. ΔE is a value which is proportional to the appearance of color as a result of the presence of apoenzyme and the DNP-FAD conjugate together with the indicator, peroxidase and glucose present in the test device. Tristimulus values from the Rapid Scanner are used to calculate ΔE according to the convention described in "Supplement No. 2 to Commission Internationale de L'Eclairage (Paris), Publication No. 15, Colorimetry, (E.-1.3.1), 1971."

TABLE A

| Visual Differentiation Between Levels Of DNP—Caproate | |
|---|---|
| DNP—Caproate (μM) | ΔE |
| 0–1 | 10.5 |
| 1–2 | 3.2 |
| 2–4 | 4.5 |
| 4–8 | 5.2 |

The data shows the usefulness of a completely unitized homogeneous immunoassay in the solid state.

EXAMPLE III

Improved Stability of Apoenzyme in a Carrier Matrix

Experimental efforts were directed towards a way of stabilizing apoglucose oxidase in a carrier matrix such as paper, thereby insuring greater reactivity, sensitivity and shelf life for the test device. Reagent strips were prepared similarily as in Example I, except that the antibody was omitted. A two-dip system was utilized whereby pieces of Eaton & Dikeman 205 paper measuring 4 cm square were impregnated with a first dip comprising TMB and acetone, dried, and reimpregnated with a second dip solution containing the other ingredients making up a reagent system sensitive to conjugate. Devices prepared in this fashion were heat-stressed and innoculated with conjugate to study the effect of bovine serum albumin (BSA) and polyvinyl alcohol (PVA) on the stability of the apoenzyme.

Two ml of a 2 mM solution of 3,3',5,5'-tetramethylbenzidine (TMB) in acetone was used to impregnate a 4 cm square piece of Eaton & Dikeman 205 filter paper. The paper was dried at 90° C. for 1–2 minutes in a forced air oven.

A second dip solution was prepared which contained tris-glutamate citrate buffer (pH 6.4) at a concentration of 0.33M (see Example I), glucose at 0.1M, 19 units/ml horseradish peroxidase, glucose oxidase apoenzyme (1.3 nmoles FAD binding sites per ml), bovine serum albumin (BSA) at 0.5 mg/ml and polyvinyl alcohol (PVA) at 10 mg/ml. The TMB-impregnated papers were then immersed in the second-dip solution momentarily, removed and dried in a forced air oven at 90° C. for about 7 minutes.

Test devices were prepared having 0.5 cm square pieces of the impregnated, dried paper mounted on the ends of biaxially oriented polystyrene strips measuring about 0.5×8.3 cm. The mounting was achieved through the use of double faced adhesive tape available from the 3M Company and known as Double-Stick. Strips prepared in this fashion were stored with silica gel desiccant in amber bottles at 4° C. prior to being subjected to heat stressing experiments.

Strips which contained BSA and PVA as well as those which did not contain these materials were subjected to heat stress by storing in the capped, desiccant-containing bottles for three days at 50° C. The performance of the stressed reagent strips was evaluated by pipetting 15 μl aliquots of a 4 μM DNP-FAD solution onto the pad and incubating for 6 minutes in a closed petri dish having a wet piece of filter paper in the bottom. The unstressed strips were inoculated as above and incubated for two minutes. After incubation the strips were analyzed using the Rapid Scanner device as described in Example I above. The Rapid Scanner information was expressed as color difference units (ΔE) using as a reference unreacted strips, i.e. those wet with only distilled water instead of the DNP-FAD conjugate. The results of the Rapid Scanner analysis of the stressed stabilized test devices appear below in Table B.

TABLE B

| BSA/PVA | ΔE Unstressed | ΔE Stressed |
| --- | --- | --- |
| None | 2.2 | 2.1 |
| BSA + PVA | 19.9 | 13.6 |

The data of Table B indicates that without the presence of BSA and PVA, the responsiveness of the strips is markedly diminished, whereas when BSA and PVA are present, a 6.5 to 9-fold increase in color difference units is realized. Moreover, the presence of BSA and PVA in the formulation markedly stabilizes the strips against heat stress. Thus, the data in this experiment show dramatic advantage in using these stabilizing agents in producing apoenzyme-based immunoassay in the solid state.

EXAMPLE IV

Application of the Model System to a Theophylline Assay

An experiment was conducted in an attempt to reduce the model system described in Examples I–III to a practical application having clinical significance, i.e. a test for theophylline. Theophylline [1,3 dimethylxanthine, c.f. *The Merck Index*, 9th ed., p. 1196(1976)] is a drug useful in the management of asthma. In most patients the therapeutic range of serum concentration lies between 10 and 20 micrograms per milliliter (μg/ml) whereas toxicity almost invariably appears at blood levels over 35 μg/ml. A test device was prepared similarly to the previous examples except that the conjugate used comprised FAD linked covalently with theophylline, and the antibody employed was partially purified antibody to theophylline.

1. Conjugate Synthesis

The conjugate molecule whereby FAD is bound covalently to theophylline was prepared as follows: 1,3-Dimethyl-1,6,7,8,-tetrahydropyrido[1,2e]-pyrine-2,4,9-[3H]-trione (0.9 mg/3.62 μmmol), prepared according to the method of Cook et al.* was added to 0.2 ml dimethylsulfoxide containing 2.4 μmol N$^6$-(aminohexyl)FAD. After 4 hours a further 1.8 mg (7.3 μmol) of the trione was added. The solution was stirred overnight, the solvent evaporated under vacuum (0.1 mm Hg), and the residue chromatographed on a column (2.5×90 cm) of Sephadex LH-20 equilibrated with 0.3M-triethylammonium bicarbonate, pH 7.8. The crude product eluting between 216 and 246 ml of effluent was collected, applied to a 20×20 cm×100 μm silica gel plate and chromatographed using ethanol/1M-triethylammonium bicarbonate, pH 7.8 (8:2 by volume). The band containing the desired product (R$_F$ 0.77) was scraped from the plate, extracted with 1M-triethylammonium bicarbonate buffer, pH 7.8, filtered and concentrated. Final purification by chromatography on Sephadex LH-20 equilibrated with 0.3M buffer gave 1.26 μmol of theorphylline-FAD as determine by the absorbance at 450 nm, which represented a yield of 53%.

*Cook, C. E., Twine, M. E., Meyers, M., Amerson, E., Kepler, J. A. & Taylor, G. F. *Res. Commun. Chem. Path. Pharmacol.* 13, 497–505, (1976).

The conjugate thus prepared has the structure depicted supra under the caption "Enzyme prosthetic group labels" in which —R—L has the structure

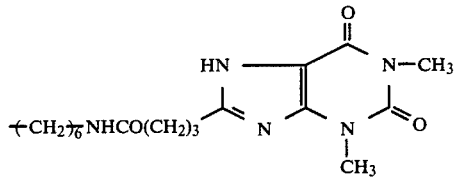

2. Preparation of the Test Device

Using this theophylline-FAD conjugate, reagent strips for the assay of theophylline were prepared. Pieces of Buckeye S-22 paper measuring 4 cm square were impregnated with a first dip solution comprising 5 mM TMB in acetone containing 0.1 gm per 100 ml of an emulsifier known as ON-870, marketed by General Aniline and Film Corporation. After dipping into the first dip solution, the impregnated papers were dried at 50° C. for 1 minute in a forced air oven. Following drying, the papers were then impregnated with a second dip solution. The second dip was an aqueous solution which as 0.33M in the buffer described in Example I to give a pH of 6.4, 0.1M in glucose, 19 units/ml of horseradish peroxidase, glucose oxidase apoenzyme (1.0 nmoles FAD binding sites per ml), partially purified antibody to theophylline (0.14 ml antibody per ml dip solution), 0.5 mg/ml bovine serum albumin and 0.5 gm of polyvinyl alcohol per 100 ml. The antiserum to theophylline was collected from rabbits immunized with a theophylline immunogen conjugate as described by Cook, et al., *Res. Comm. Chem. Path. Phamacol.* 13: 497–505 (1976). The serum was partially purified as in Example I. After brief immersion of the dried papers in the second dip solution, a second drying was effected at 50° C. for 12 minutes in a forced air oven.

The doubly impregnated papers were then further impregnated with a third solution containing FAD-theophylline conjugate at a concentration of 0.5 μM in acetone. These papers were then dried at 50° C. for 1 minute in the forced air oven.

Test devices were prepared having 0.5 cm squares of the triply impregnated papers mounted on strips of polystyrene measuring 0.5×8.3 cm utilizing double-faced adhesive known as Double-Stick (3M Company).

Figure 3:
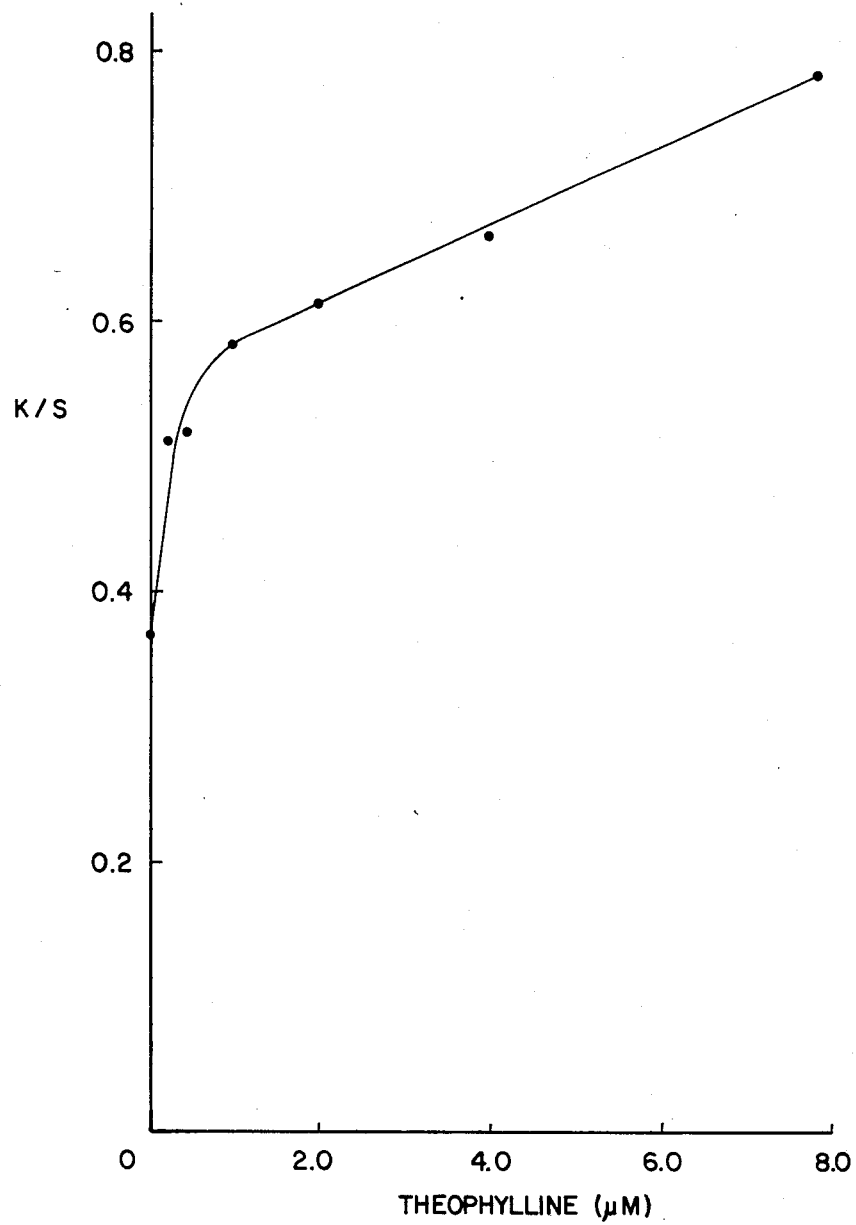

To test the performance of the test devices prepared above, solutions of theophylline in water were prepared having concentrations of theophylline in the range of 0–8 μM. The devices were dipped in these solutions and, after an incubation period of 2 minutes, were analyzed in the Rapid Scanner described in Example I. The dose-response curve is shown in FIG. 3 wherein K/S is plotted against theophylline concentration.

The plotted data shows that there is an observable color intensity change for varying amounts of theophylline in solution, and that the change is indicative of the particular theophylline concentration.

EXAMPLE V

Application of the Model System to a Phenytoin Assay

As in Example IV, an experiment was conducted to adapt the model system of Examples I–III to an assay for a clinically significant analyte: phenytoin. The experiment demonstrated the adaptability of a homogeneous prosthetic group-labeled immunoassay to a dry reagent strip format for phenytoin detection. As in the previous Examples, the carrier matrix format permitted simultaneous competition between prosthetic group-labeled phenytoin and the analyte (phenytoin) for binding to an antibody for phenytoin.

1. Phenytoin-FAD Conjugate Synthesis

To 14.7 mg (40.0 μmol) of 5-(2'-carboxybutyloxyphenyl-5-phenylhydantoin in 1.8 ml of molecular sieve-dried dimethylformamide (DMF), under argon, was added 0.10 ml (40.0 μmol) of a 400 μM solution of isobutyl chloroformate in DMF. The reaction was stirred one hour at room temperature. To the reaction mixture was added a solution of 10.0 μmol of $N^6$(aminohexyl)FAD in 2.0 ml of molecular sieve-dried dimethylsulfoxice (DMSO), followed by 0.05 ml of a 400 μM solution of triethylamine in DMF. The mixture was stirred 19 hours at room temperature, then was diluted to 450 ml with water and was applied to a 1.5×30 cm column of Whatman DE-52 cellulose anion exchange resin (bicarbonate form) with the aid of a peristaltic pump. The colum was then eluted with a gradient of 1.5 liters of water to 1.5 liters of 0.3M triethylammonium bicarbonate aqueous solution. Fractions of approximately 16 ml were collected with fractions 70–88 determined as containing the product on the basis of activity with apoglucose oxidase. These fractions were combined and the solution adjusted to pH 7. The yield was determined as 4.78 μmol (47.8% yield) on the basis of the absorbance of the solution at 450 nm using the millimolar extinction coefficient of $FAD(E_{450}=11.3)$.

2. Preparation of Test Devices

The test devices were prepared by consecutive immersion of a piece of paper into 3 solutions, each of which contained different components of an immunoassay system potentially responsive to the presence of phenytoin, with drying between each immersion. Accordingly, a piece of paper measuring 4 cm square (S-22, Buckeye Cellulose Corp, Memphis, TN) was immersed in a 5 mM solution of TMB in acetone containing 0.1% (w/v) of an emulsifier known as ON-870 (General Aniline & Film Corp.). After drying at 50° C. for 1 minute, the paper was immersed in a second, aqueous, solution which was 0.2M in tris-glutamate buffer, pH 6.4, 0.1M in glucose, horseradish peroxidase (19 units/ml), apoglucose oxidase (1.0 n moles FAD binding sites /ml), 0.5 mg/ml bovine serum albumin, 0.5 g/100 ml polyvinyl alcohol (see Example III), and antiphenytoin serum (0.14 ml antiserum per ml). The antiserum was raised against o-caproyldiphenylhydantoin, similarly as in Example IV.

After drying at 50° C. for 12 minutes in a forced air oven, the paper was impregnated by immersion in a third solution containing the FAD-phenytoin conjugate (0.5 μm) in n-propanol with 0.1 g/100 ml Gafquat 734, a polymer having pendant quaternary amine groups (General Aniline & Film Corp.).

Following drying at 50° C. for 3 to 4 minutes, the impregnated paper was used to make test strips having a 0.5 cm square of the reagent-laden paper mounted at one end of a strip of biaxially oriented polystyrene film measuring 0.5 by 8.3 cm. Mounting was achieved using a double-faced adhesive tape known as Double-Stick (3M Company).

Figure 4:
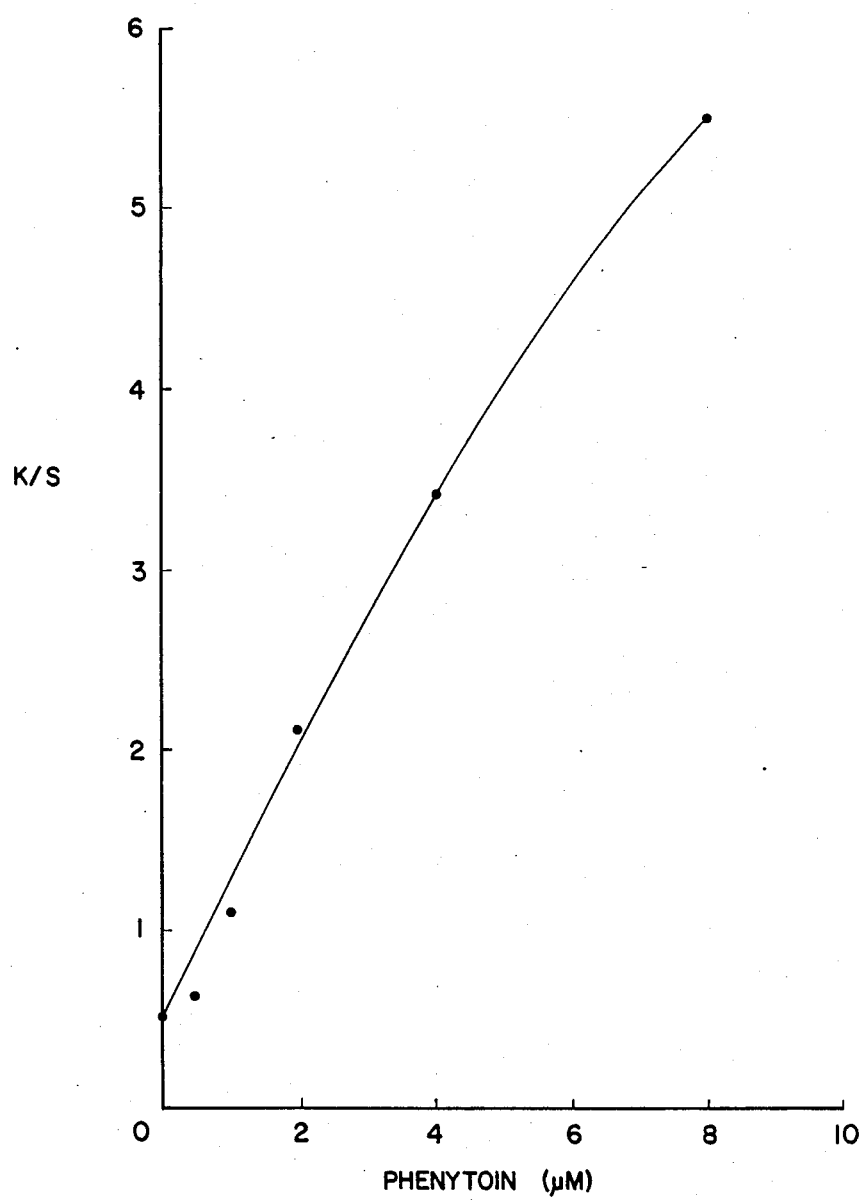

In order to assess the utility of these test devices for response to the presence of phenytoin, they were innoculated with test solutions containing the analyte at concentrations ranging from 0 to 8 μM and analyzed in the Rapid Scanner 2 minutes after innoculation. FIG. 4 shows the change in K/S with respect to phenytoin concentrations of 0, 0.5, 1, 2, 4 and 8 μM in water.

The data presented in FIG. 4 shows that the test device responds well to the presence of phenytoin, enabling facile determination of different concentrations of the analyte.

EXAMPLE VI

Application of the Unitized Model System to a Fluorescence Immunoassay Test Device An experiment was conducted to explore the applicability of the unitized model system of Example II to fluorescence immunoassays. Accordingly, a test device was prepared as in Example II wherein p-hydroxyphenylacetic acid was substituted for TMB. Oxidation of p-hydroxyphenylacetic acid by peroxide in the presence of peroxidase results in a fluorometrically detectable product.

The device was prepared as follows: A piece of Buckeye S-22 paper was impregnated with a solution comprising

| | |
|---|---|
| Tris-glutamate buffer (1 M, pH 6.4) | 0.8 ml |
| Glucose (1 M aqueous solution) | 0.4 ml |
| Horseradish peroxidase (153 units/mg, 1.25 mg/ml) | 0.4 ml |
| Polyvinyl alcohol (5 g/100 ml) | 0.4 ml |
| Bovine serum albumin (20 mg/ml) | 0.1 ml |
| Gafquat 734 (10 g/100 ml water, see Example V) | 0.2 ml |
| Apoglucose oxidase (40 nmoles FAD binding sites/ml | 0.16 ml |
| Partially purified DNP—antibody (see Example I) | 0.54 ml |
| p-Hydroxyphenylacetic acid (80 mM in water) | 0.04 ml |
| Distilled water | 0.96 ml |

Following impregnation the paper was dried in an air oven at 50° C. for 22 minutes.

The dried paper was impregnated with a 2 μM solution of DNP-FAD conjugate in n-propanol and dried at 50° C. for five minutes.

Metallic Mylar tape (3M Company) was applied to one side of the dried reagent paper. The paper was mounted on biaxially oriented polystyrene film using Double-Stick adhesive tape applied to the Mylar layer. The resultant test device comprised a 0.2 by 0.4 inch piece of Mylar-backed reagent paper mounted on a polystyrene strip measuring 0.2 by 3.5 inches.

As a control device for comparison with the test device, unimpregnated paper was similarly applied with Mylar and Double-Stick to polystyrene strips.

The fluorescent strips were examined as to their performance using a photomultiplier. A quartz fiber optic was positioned at a 45° angle to the plane of the device to be examined. This fiber optic was equipped with a mercury lamp and an excitation band-pass filter at 314 nm. The fluorescence of a given device was obtained directly from another fiber optic positioned 45° to the plane of the sample device, and provided with an interference filter (420 nm). The intensity was read in millivolts using a photomultiplier.

Figure 5:
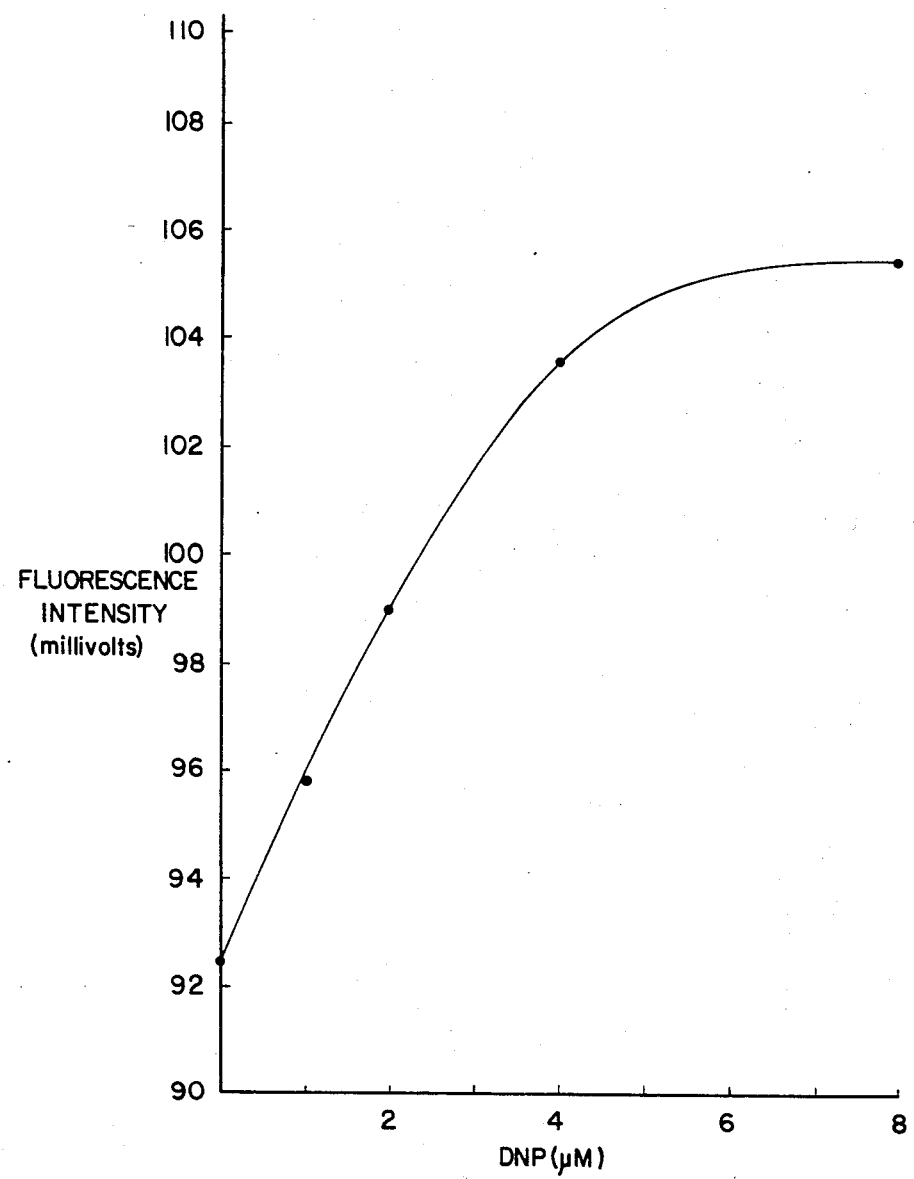

To test the efficacy of the fluorescent test devices, 30 μl aliquots of DNP-containing test solutions were pipetted onto the reagent paper portions, and permitted to incubate for 11 minutes at room temperature in a humidity chamber. The DNP test solutions varied in concentration from 0 to 8 μM DNP. Fluorescence intensity was measured for 0, 1, 2, 4 and 8 μM solutions using the photomultiplier apparatus. The measurement was duplicated using the control devices. FIG. 5 shows the dose-response relationship for the test devices. Data from the control devices assured that the data in FIG. 5 was not influenced by any intrinsic fluorescence of the DNP analyte.

This experiment conclusively demonstrates the successful application to a solid phase device of a homogeneous immunoassay technique using fluorescence as the detectable response.

B. ENZYME SUBSTRATE-LABELED IMMUNOASSAY TEST DEVICES

EXAMPLE VII

Paper Multilayer Element

In the experiment described by this example, an integral multilayer analytical element was prepared and tested for its ability to quantitatively determine, as read by front face fluorometry, the presence of the ophylline in a liquid sample.

Antiserum Preparation

Antiserum to theophylline was prepared by the method described in pending U.S. Ser. No. 87,819, filed Oct. 23, 1979 and assigned to the present assignee, hereby incorporated by reference.

Conjugate Preparation

Galactosyl-umbelliferone-theophylline (conjugate) was prepared by the method described in aforesaid pending U.S. Ser. No. 87,819.

Element Preparation

The solution used in preparing one layer of the theophylline specific element contained the following components:

| Component | Quantity |
| --- | --- |
| water | 27 μl |
| 0.1 M Bicine buffer (pH 8.5) | 20 μl |
| theophylline antisera | 100 μl |
| β-galactosidase (78 U/ml)* | 3 μl |

*Units are defined in Clin. Chem. 23:1402(1977)

A 3×1.2 cm layer of Whatman 31 ET paper (Whatman, Inc., Clifton, N.J.) was mounted, by double-faced adhesive tape, on a 8.2×1.2 cm polystyrene support and then the above prepared solution was pipetted onto the layer of Whatman 31 ET paper. The paper was dried in a convection oven at 50° C. for 10 minutes.

A second solution was then prepared by dissolving the conjugate into 50 μl of water to a final concentration of 14.4 μM for this solution. The solution so prepared was then pietted onto a 1.0×3.0 cm layer of Whatman 54 paper. This impregnated layer was then dried in a convection oven at 50° C. for 10 minutes.

The second layer was then fixed at one edge to the first by a strip of double-faced adhesive tape.

Test Solution

Theophylline was added to aliquots of 0.05M Bicine buffer, pH 8.5, to give final theophylline concentrations of 0.5, 1.0, 2.5, 5.0 and 40 micrograms per milliliter (μg/ml), respectively.

Analytical Procedure

The analytical elements which had been prepared and fixed to the supports as described above were each inserted into a mechanical holder suitable for vertical positioning the device in a fluorometer. Just prior to inserting the element and holder into the fluorometer, a 250 μl aliquot of one of the theophylline solutions, prepared as described above, was pipetted onto the exposed surface of the conjugate-containing layer.

The fluorometer had been adjusted to provide an excitation light source of 405 nm wavelength, which struck the surface of the element at a 60° angle from the normal to the surface, and to detect light emitted at a wavelength of 450 nm. A front face measurement of fluorescence was made at a 30° angle from the normal to the pad.

The fluorescence response of each sample was first measured over time (0–200 seconds) and then readings of each were taken at 200 seconds.

Results

Figure 6:
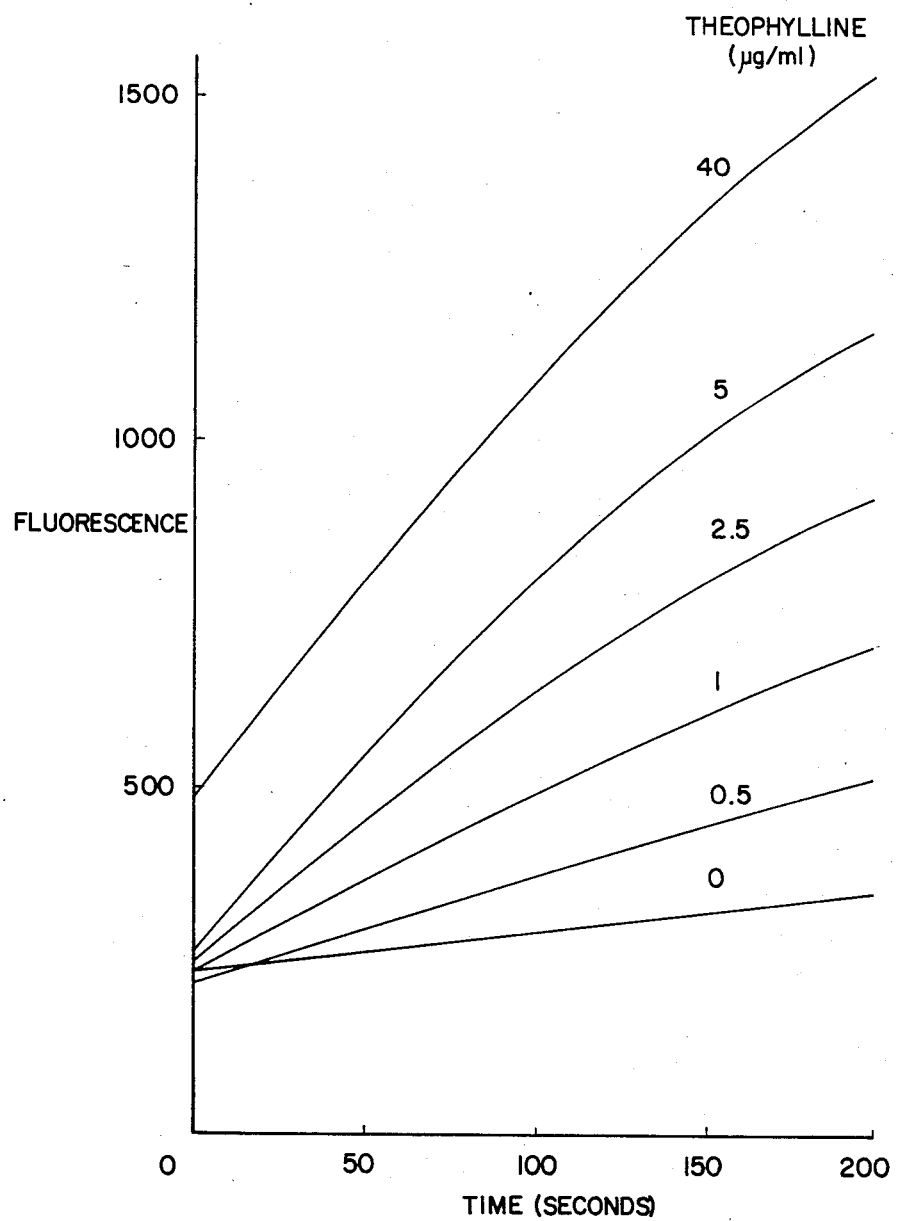
Figure 7:
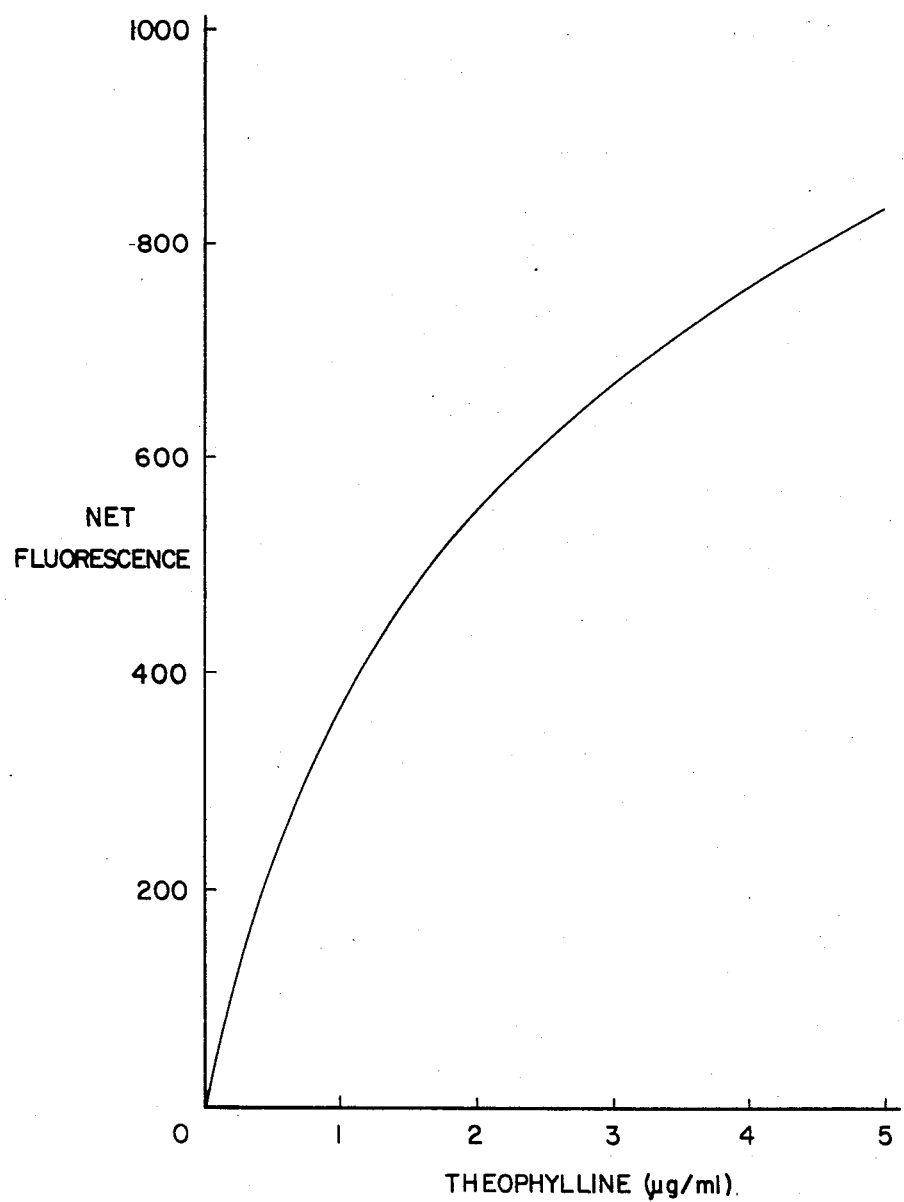

The readings obtained by this analytical procedure were in the form of relative fluorescence. The relative fluorescence observed was compared to the amount of theophylline present in the sample administered. The fluorescence response with time is shown in FIG. 6. The fluorescence at 200 seconds was plotted as a function of theophylline concentration to provide the theophylline standard curve of FIG. 7.

Conclusion

The resultant data shows the integral analytical element to provide a quantitative detectable response to the theophylline concentration of each of the aliquots tested. Inhibition of the reaction was caused by the presence of antibody to theophylline. Increasing concentration of theophylline overcame the inhibition resulting in a theophylline dependent increase in the generation of fluorescent product.

EXAMPLE VIII

Freeze Dried Element

In the experiment reported by this example a single layer element for theophylline determination was achieved using temperature control techniques to prevent untimely interaction of reagents.

Antiserum Preparation

Antiserum to theophylline was prepared by the method described in the aforesaid pending U.S. Ser. No. 87,819. This antiserum was precipitated with aqueous ammonium sulfate, 33 milligrams/deciliter (mg/dl), the precipitate was dissolved in and dialyzed against 0.05M Bicine buffer (pH 8.5) and a theophylline antibody concentrate was obtained. This concentrate contained approximately 200 μmol of theophylline binding sites per milliliter.

Conjugate Preparation

Galactosyl-umbelliferone-theophylline (conjugate) was prepared by the method described in the aforesaid pending U.S. Ser. No. 87,819.

Element Preparation

The first solution used in preparing the monolayer theophylline specific element contained the following components:

| Component | Quantity |
| --- | --- |
| 0.5 M Bicine buffer (pH 8.5) | 10 μl |
| theophylline antibody concentrate | 150 μl |

| Component | Quantity |
| --- | --- |
| β-galactosidase (88 U/ml) | 40 µl |

A 0.5×1.0 cm layer of Whatman 31 ET paper (Whatman, Inc., Clifton, NJ) was mounted by double-faced adhesive tape, on a 8.2×0.5 cm polystyrene support and then 20 µl of above prepared solution was pipetted onto the layer of Whatman 31 ET paper. The paper was dried in a convection oven at 50° C. for 10 minutes and then precooled on dry ice for five (5) minutes in a low humidity room.

A 6.13 millimolar (mM) solution of theophylline-umbelliferone-galactose in dimethylsulfoxide (DMSO) was diluted to a 0.077 mM solution in water and 20 µl was applied to each of the paper layers which had been treated as described above. The elements were freeze dried overnight.

Test solution

Theophylline was added to aliquots of 0.05 molar (M) BIcine buffer to give final theophylline concentrations of 0.0, 4.0, 16.0 and 40 µg/ml, respectively.

Analytical Procedure

The analytical elements which had been prepared and fixed to supports as described above were each inserted into a mechanical holder suitable for horizontally positioning the device in a reflectance photometer. Just prior to inserting the element and holder into the reflectance photometer a 50 µl aliquot of one of the theophylline solutions, prepared as described above, was pipetted onto the exposed surface. The photometer had been adjusted to follow changes in reflectance at 400 nanometers.

The reflectance of each was first measured over time (0-200 seconds) and then readings of each were taken at 200 seconds.

Results

Figure 8:
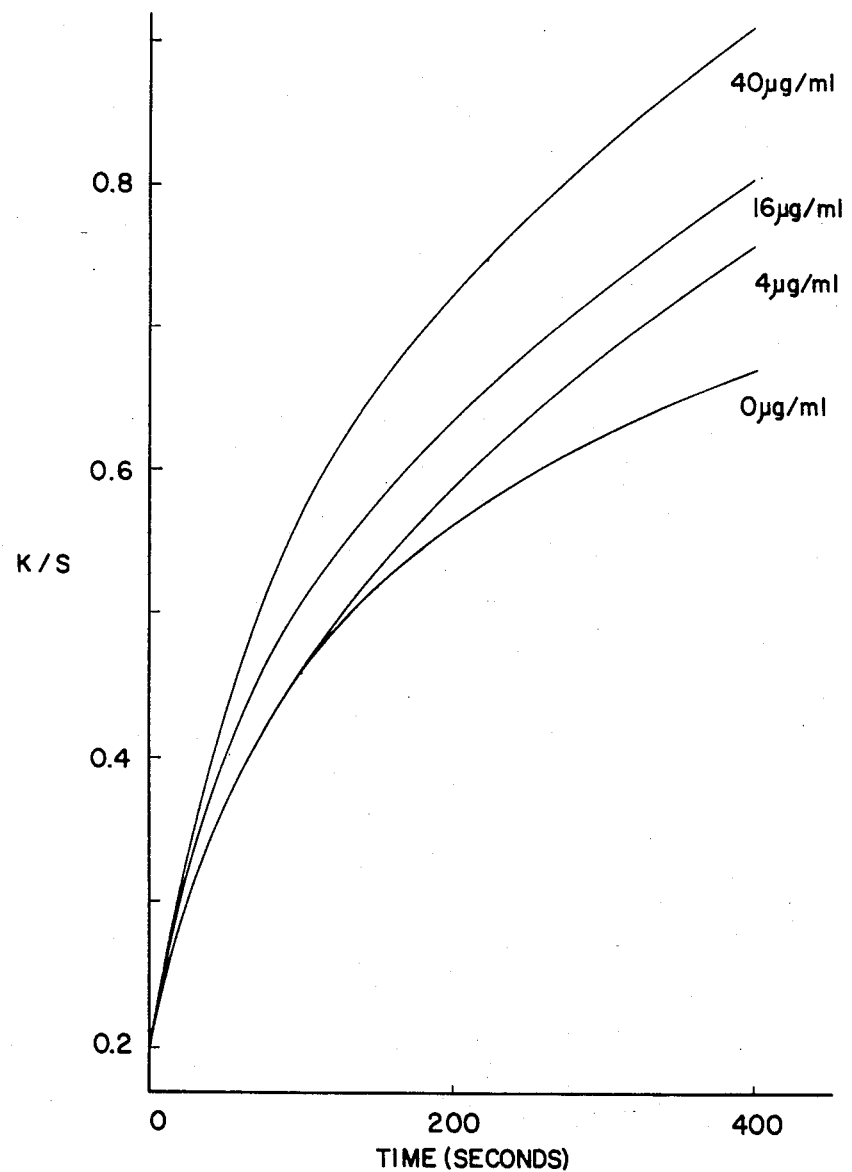

The data obtained by the above-described procedure is graphically illustrated by FIG. 8. The ordinate units (K/S) are defined as in Example II.

Conclusion

The resultant data shows the integral analytical element to provide a quantitative chromogenic response to the theophylline concentration of each of the aliquots tested.

Under these conditions, the reaction is inhibited by the presence of antisera and this inhibition is progressively overcome by increasing concentrations of theophylline.

EXAMPLE IX

Multiple Impregnation Element

In the experiment described by this example, a single layer element was prepared and tested for its ability to quantitatively determine, as read by front face fluorometry, the presence of theophylline in a liquid sample.

Antiserum Preparation

Antiserum to theophylline was prepared by the method described in the aforesaid pending U.S. Ser. No. 87,819.

Conjugate Preparation

Galactosyl-umbelliferone-theophylline (conjugate) was prepared by the method described in the aforesaid pending U.S. Ser. No. 87,819.

Element Preparation

The solutions used in preparing the theophylline specific element contained the following components:

| Component | Quantity |
| --- | --- |
| Aqueous solution | |
| theophylline antiserum | 400 µl |
| 0.5 M Bicine buffer, pH 8.5 | 160 µl |
| water | 35 µl |
| β-galactosidase (132.7 U/ml) | 5 µl |
| Organic solution | |
| methylene chloride | 1.00 ml |
| conjugate (771 µM in DMSO) | 4.2 µl |

A 1×1 cm layer of Whatman 31 ET paper was laminated onto silver Mylar (3M Co.) and mounted, by double-faced adhesive tape, on a 8.3×1 cm polystyrene support and then the above prepared aqueous solution was pipetted onto the layer of Whatman 31 ET paper. Other underlying reflective layers, such as those which are silvered or opaque, are likewise suitable. The paper was dried in a convection oven at 50° C. for 15 minutes. The organic solution was then pipetted onto the paper containing the dried residue of the aqueous solution and dried in a convection oven at 50° C. for 15 minutes.

Test Solution

Theophylline was added to aliquots of water to given final theophylline concentrations of 0.125, 0.25, 0.50, 1.00, 10.0, 20.0 and 40.0 µg/ml, respectively.

Analytical Procedure

The analytical elements which had been prepared and fixed to supports as described above were inserted into a mechanical holder suitable for horizontally positioning the device in a fluorometer. Just prior to inserting the element and holder into the fluorometer, a 70 µl aliquot of one of the theophylline solutions, prepared as described above, was pipetted onto the exposed surface of the element.

The fluorometer had been adjusted to provide an excitation light source at 405 nm, which struck the surface of the element at a 90° angle, and to detect light emitted at a wavelength of 450 nm. A front face measurement of fluorescence was made at a 90° angle from the pad.

The fluorescence response of each was first measured over time (0-6 minutes) and then readings of each were taken at 6 minutes.

Results

Figure 9:
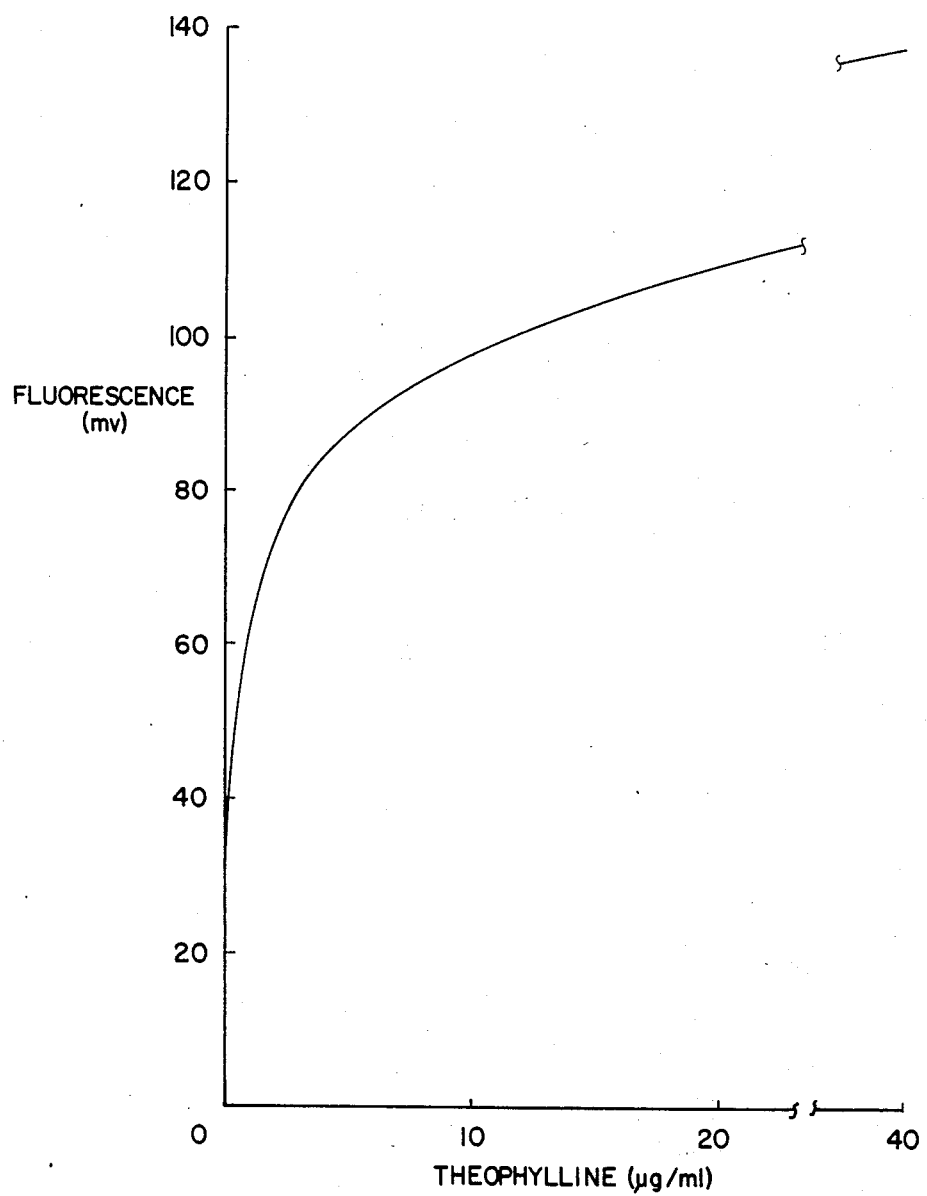
Figure 10:
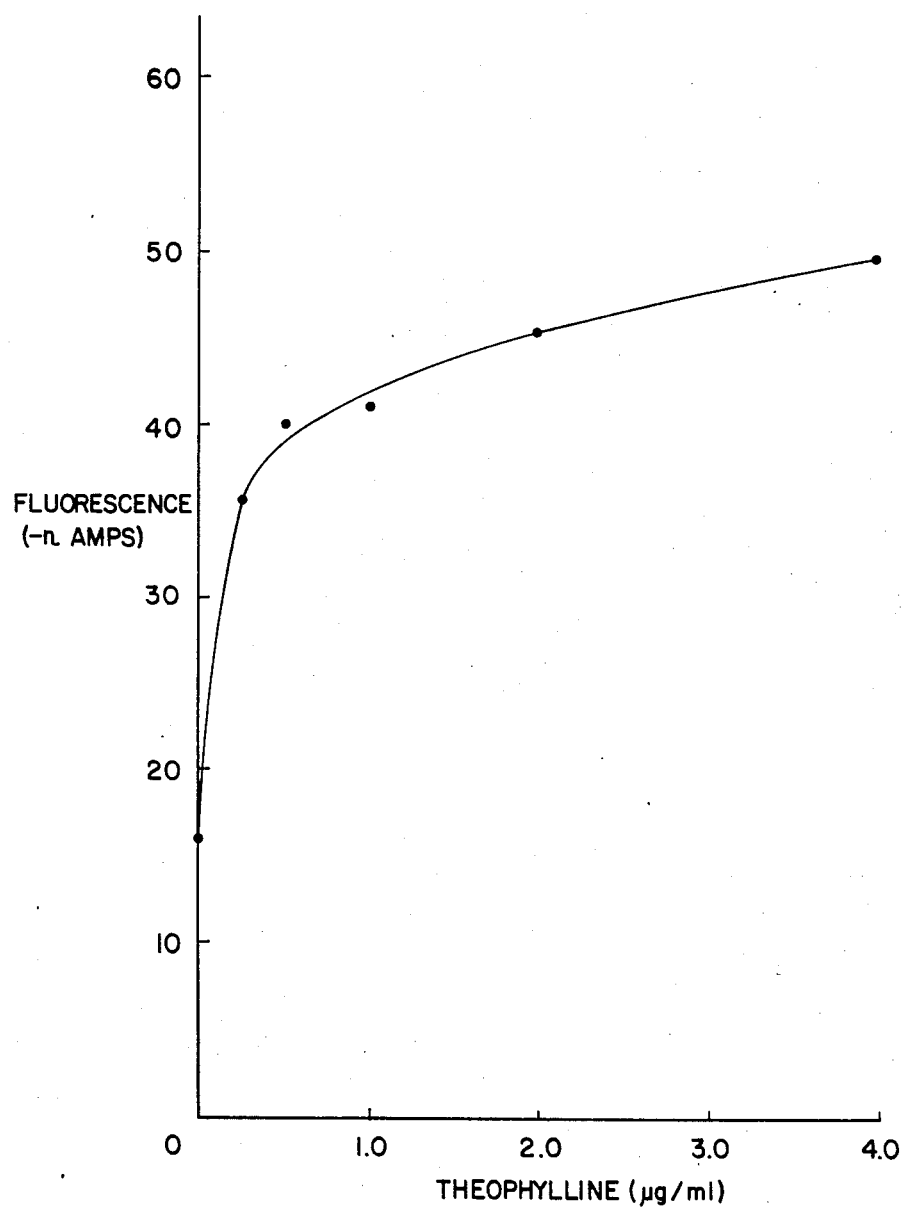
Figure 11:
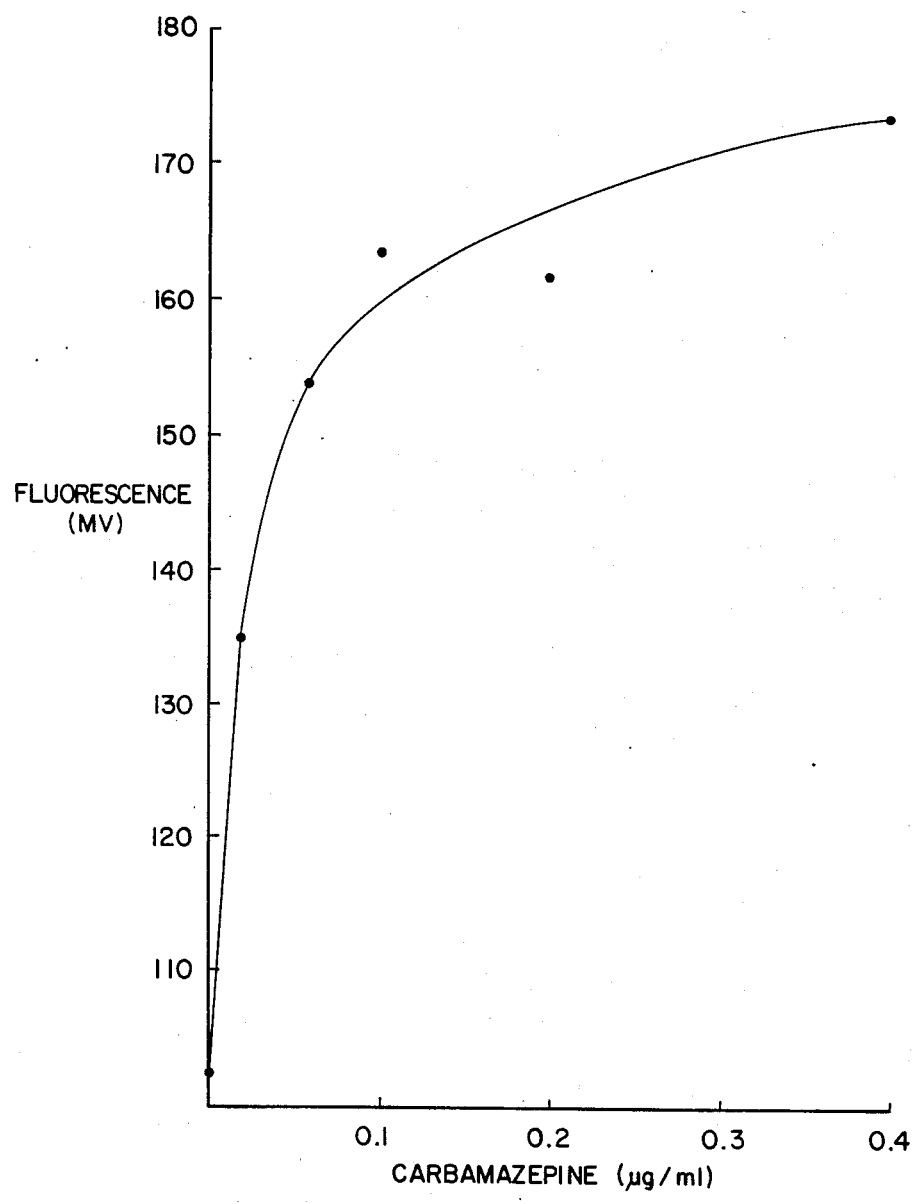
Figure 12:
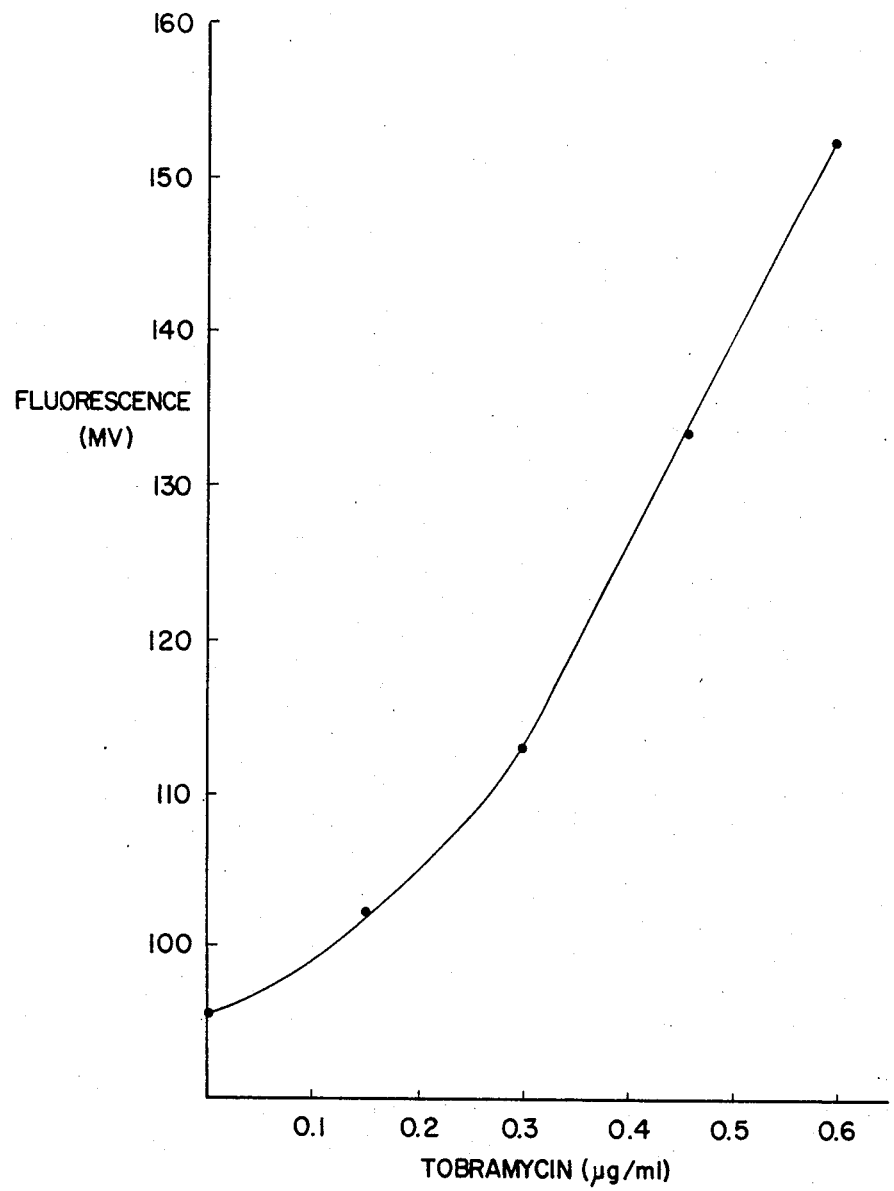
Figure 13:
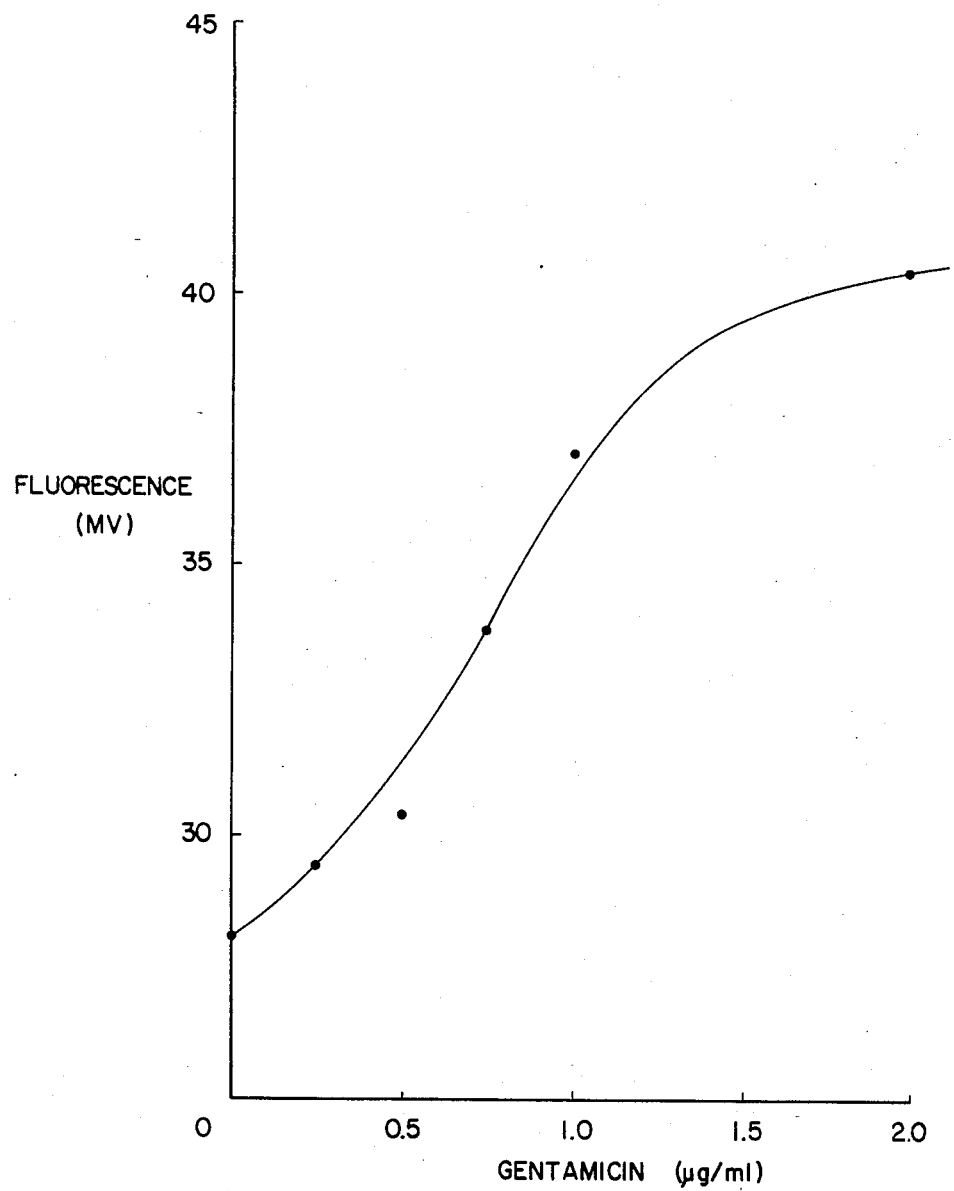

The data obtained in the above described procedure is graphically illustrated in FIG. 9. The ordinate units are expressed as millivolts.

Conclusion

The resultant data show the analytical element to provide a quantitative detectable response to the theophylline concentration of each of the aliquots tested.

Under these conditions, the reaction is inhibited by the presence of antiserum and this inhibition can be progressively overcome by increasing concentrations of theophylline.

EXAMPLE X

Reversible Complex Formation Element

In the experiments described by this example, single layer elements were prepared and tested for their ability to quantitatively determine, as read by front face fluorometry, the presence of theophylline, carbamazepine, tobramycin and gentamicin. The therapeutic range of serum concentration and minimum toxic levels of each drug are summarised in the following table:

| Drug | Therapeutic Range | Toxicity Levels |
| --- | --- | --- |
| Theophylline | 10–20 µg/ml | 35 µg/ml |
| Carbamazepine | 4–12 µg/ml | 15 µg/ml |
| Tobramycin | 5–10 µg/ml | 12 µg/ml |
| Gentamicin | 5–10 µg/ml | 12 µg/ml |

Antisera Preparation

Antisera to theophylline, carbamazepine, tobramycin and gentamicin were prepared by the methods described in the aforementioned pending U.S. Ser. No. 87,819.

Conjugate Preparation

Galactosyl-umbelliferone-theophylline, galactosyl-umbelliferone-carbamazepine, galactosyl-umbelliferone-tobramycin and galactosyl-umbelliferone-sisomicin (an analog of gentamicin) were prepared by the methods described in the aforementioned pending U.S. Ser. No. 87,819.

Element Preparation

Solutions used in preparing one layer of the theophylline, carbamazepine, tobramycin and gentamicin specific elements contained the components shown in Table C.

1×1 cm layers of Whatman 31 ET paper (Whatman, Inc., Clifton, NJ) were laminated onto silver Mylar and mounted by double-faced adhesive tape on 8.3×1 cm polystyrene supports and then the above prepared solutions were pipetted onto the layers of Whatman 31 ET paper. The papers were dried in a convection oven at 50° C. for 15 minutes.

Test Solutions

Theophylline, carbamazepine, tobramycin and gentamicin were added to aliquots of water to give samples within the final concentration ranges summarized below.

| Drug | Concentration Range |
| --- | --- |
| Theophylline | 0–4.0 µg/ml |
| Carbamazepine | 0–0.4 µg/ml |
| Tobramycin | 0–0.6 µg/ml |
| Gentamicin | 0–2.0 µg/ml |

Analytical Procedure

The analytical elements which had been prepared and fixed to supports as described above were placed in a chamber suitable for maintaining a constant humidity. Prior to closing the chamber, 70 µl aliquots of drug solutions prepared as described above, were pipetted onto the exposed surface of the respective analytical elements.

TABLE C

| Component | Theophylline element | Carbamazepine element | Tobramycin element | Gentamicin element |
| --- | --- | --- | --- | --- |
| antisera | 100 µl | 100 µl | 100 µl | 100 µl |
| conjugate | 1.7 µl | 1.2 µl | 3.4 µl | 19.2 µl |
| (concentration) | (771 µM in DMSO) | (936 µM in DMSO) | (294 µM in formic acid) | (678 µM in formic acid) |
| 0.5 M Bicine buffer (pH 8.5) | 40 µl | 40 µl | 40 µl | 40 µl |
| water | 53.4 µl | 53.9 µl | 51.7 µl | 35.9 µl |
| β-galactosidase | 4.9 µl | 4.9 µl | 4.9 µl | 4.9 µl |

The fluorescence generated at room temperature at the end of 15 minutes was measured in a fluorometer equipped with a mechanical holder suitable for horizontally positioning the analytical element. The fluorometer had been adjusted to provide excitation light source at 405 nm, which struck the surface at 90° and to detect light emitted at a wavelength at 450 nm. A front face measurement of fluorescence was made at a 90° angle from the pad.

Results

The data obtained by the above-described procedure is graphically illustrated by FIGS. 10, 11, 12 and 13 for theophylline, carbamazepine, tobramycin and gentamicin, respectively. The ordinate units are expressed in terms of electrical output.

Conclusion

The resultant data show the integral analytical elements to provide quantitative detectable responses to the concentration ranges of the respective drugs. Increasing concentrations of theophylline, carbamazepine, tobramycin and gentamicin results in a drug dependent increase in fluorescence of the respective analytical elements. The techniques used in the experiments described have made it possible for all components to be incorporated into a single element.

EXAMPLE XI

Film Multilayer Element

In the experiment described in this example, an integral double layer analytical element was prepared using two films containing assay components for the substrate labeled fluorescent immunoassay. The element was tested for its ability to quantitate theophylline by front facefluorometry.

Antisera and Conjugate Preparation

The preparation of antisera and conjugate was as described in Example VII.

Element Preparation

The following stock solutions were used:

2% Agarose (Miles #49-051) in 0.05M Bicine buffer pH 8.5. Sample brought into solution at 100° C., then thermostated at 60°.

10% Triton X100

β-galactosidase, 86 Units/ml in 0.5M Bicine buffer pH 8.5

6.67% Polyvinylpyrrolidone (Aldrich #85,647-9, average MW 360,000) in chloroform Galactosyl-umbelliferone-theophylline (conjugate), 6.16 mM in dimethylsulfoxide.

Theophylline antisera and β-galactosidase were incorporated into the agarose solution at 60° C. to provide a composition having the formulation:

| Component | Quantity |
| --- | --- |
| Agarose solution | 0.25 ml |
| Theophylline antisera | 0.75 ml |

-continued

| Component | Quantity |
|---|---|
| β-galactosidase | 0.03 ml |
| Triton X100 | 0.01 ml |

The antisera was prewarmed to 60° C. prior to mixing. A 2.5 cm wide film was spread over a polyester sheet (3M Co., Type 2352) using a conventional doctor blade set for a film thickness of 0.5 cm. After gelation, the film was dried at 47° C. for 10 minutes.

A second film was spread over the first using a doctor blade set at 0.005 cm. The film contained conjugate in a solution of polyvinylpyrrolidone (PVP) in chloroform, this having the following formulation:

| Component | Quantity |
|---|---|
| PVP in chloroform | 0.4 ml |
| Chloroform | 0.6 ml |
| Conjugate Solution | 0.015 ml |

The film was dried at room temperature. The polyester sheet was mounted onto silvered Mylar by double-faced adhesive tape. Segments of 0.5×1 cm of this material were mounted on a polystyrene carrier; again using double-faced adhesive.

Test-Solution

Theophylline was added to aliquots of 0.05M Bicine buffer, pH 8.5 to give the final theophyllin concentrations of 1, 2, 4, 8 and 40 μg/ml.

Analytical Procedure

A volume of 30μ liters of one of the test solutions was applied to the analytical elements, described above and the fluorescence response was measured after five minutes. Fluoroescence was measured as described in Example X.

Results

Figure 14:
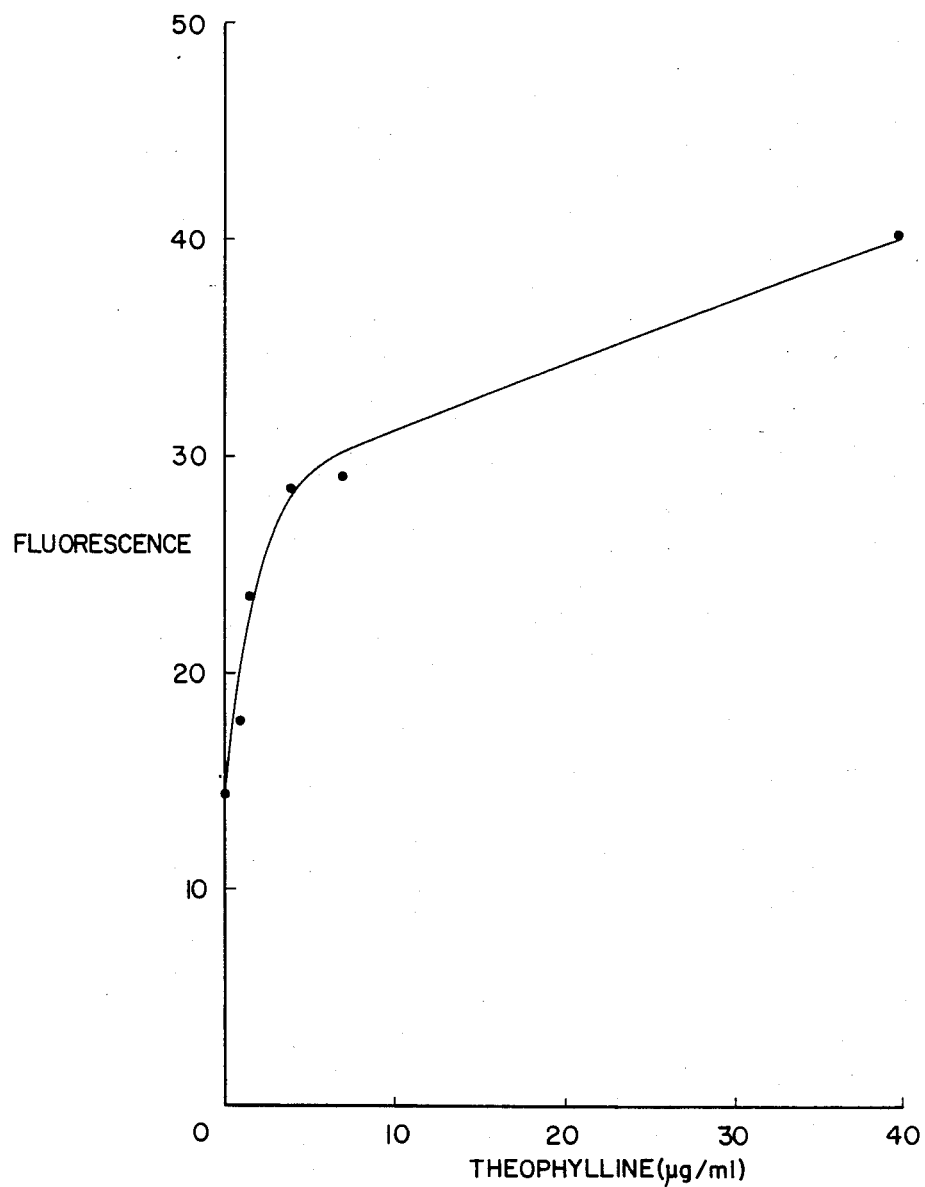

The data obtained in the above described procedure are graphically illustrated in FIG. 14. Fluorescence in arbitrary units is plotted vs. theophylline concentration.

Conclusion

The results show that incompatible reagents of an immunoassay can be preassembled into an analytical element using multilayer films which do not result in premature reaction of assay constituents and which permit quantitative detection of analytes after addition of the sample.

C. FLUORESCENCE QUENCHING IMMUNOASSAY TEST DEVICES

EXAMPLE XII

In the experiment described by this example, a single layer element was prepared and tested for its ability to perform a direct quenching fluoroimmunoassay which quantitatively determined, as read by front face fluorometry, the presence of theophylline in a liquid sample.

Antiserum Preparation

Antiserum to theophylline was prepared by the method described in the aforementioned pending U.S. Ser. No. 87,819.

Conjugate Preparation

Umbelliferone-theophylline (conjugate) was prepared by hydrolysis of galactosyl-umbelliferone-theophylline (GUT) by β-galactosidase. GUT was prepared by the method described in the aforementioned pending U.S. Ser. No. 87,819.

Element Preparation

The solutions used in preparing the theophylline specific element contained the following components:

| Component | |
|---|---|
| Aqueous solution | |
| Theophylline antisera | 50 μl |
| water | 30 μl |
| 0.5 M Bicine, pH 8.5 | 20 μl |
| Organic solution | |
| toluene | 1.00 ml |
| conjugate (0.16 mM stock in toluene) | 4 μl |

A 1×1 cm layer of Whatman 31 ET paper was laminated onto silver Mylar and mounted, by double-faced adhesive tape, on a 8.3×1 cm polystyrene support and then 20 μl of the above prepared aqueous solution was pipetted onto the layer of Whatman 31 ET paper. Other underlying reflective layers, such as those which are silvered or opaque, are likewise suitable. The paper was dried in a convection oven at 40° C. for 20 minutes. The organic solution (20 μl) was then pipetted onto the paper containing the dried residue of the aqueous solution and dried in a convection oven at 50° C. for 15 minutes.

Test Solution

Theophylline was added to aliquots of water to give final theophylline concentrations of 0.125, 0.25, 0.50, 1.00, 10.0, 20.0 and 40.0 μg/ml, respectively.

Analytical Procedure

The analytical elements which had been prepared and fixed to supports as described above were inserted into a mechanical holder suitable for horizontally positioning the device in a fluorometer. Just prior to inserting the element and holder into the fluorometer, a 70 μl aliquot of one of the theophylline solutions, prepared as described above, was pipetted onto the exposed surface of the element.

The fluorometer had been adjusted to provide an excitation light source at 405 nm, which struck the surface of the element at a 90° angle, and to detect light emitted at a wavelength of 450 nm. A front face measurement of fluorescence was made at a 90° angle from the pad.

The fluorescence response of each was measured after 2 minutes.

Results

Figure 15:
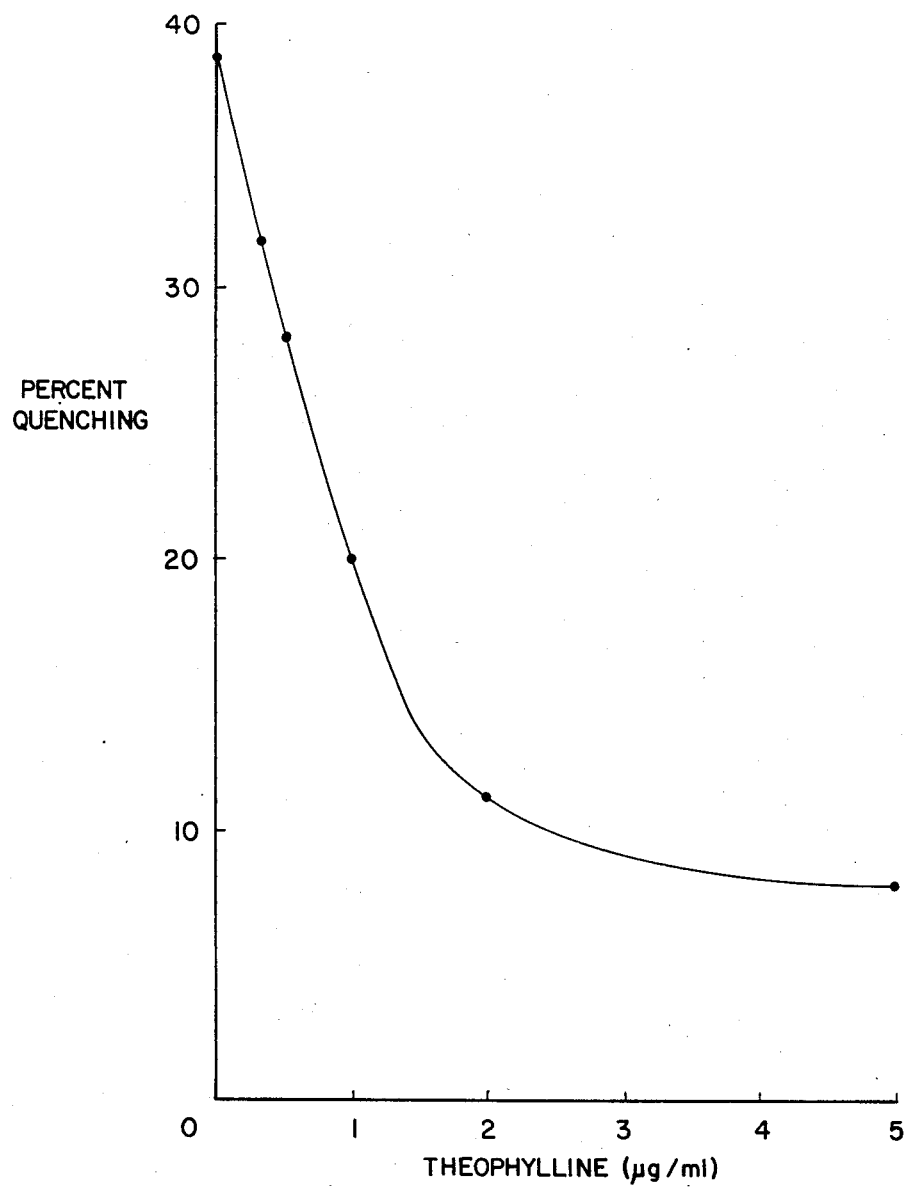

The data obtained in the above described procedure is graphically illustrated by FIG. 15. The ordinate units are expressed as percent quenching.

Conclusion

The resultant data shows the analytical element to provide a quantitative detectable response to the theophylline concentration of each of the aliquots tested.

Under these conditions, fluorescence is quenched in the presence of antiserum and this quenching can be progressively overcome by increasing the concentration of theophylline.

D. ENZYME-LABELED IMMUNOASSAY TEST DEVICES

EXAMPLE XIII

In the experiment reported by this example a multilayer element was prepared to contain all of the constituents necessary to perform an enzyme-labeled homogeneous immunoassay for theophylline.

Antiserum

Antiserum to theophylline was obtained from an EMIT ®-aad theophylline test kit purchased from Syva Company, Palo Alto, Calif.

Conjugate Preparation

G6PDH-theophylline (conjugate) was likewise obtained from an EMIT-aad theophylline test kit.

Element Preparation

The solution used in preparing one layer of the theophylline specific element was that referred to as Reagent A (containing antiserum to theophylline and enzyme substrate) in the EMIT-aad theophylline test kit from Syva Company.

A 0.5×1.0 centimeter (cm) layer of Whatman 54 paper (Whatman, Inc., Clifton, NJ) was mounted, by double-faced adhesive tape, on a 8.2×0.5 cm polystyrene support and then 10 µl of the above solution was pipetted onto the layer of Whatman 31 ET paper. The paper was dried in a convection oven at 50° C. for 10 minutes.

A second solution was then prepared by mixing equal volumes of a diaphorase/p-iodonitrotetrazolium violet (INT) solution (1.5 mg diaphorase and 1 mg INT in 2.5 ml of 0.055M tris-(hydroxymethyl)aminomethane buffer, pH 7,9) and the solution referred to as Reagent B in the EMIT-aad kit (containing the enzyme-labeled theophylline conjugate). 20 µl was pipetted onto a 0.6×1.0 cm layer of Whatman 54 paper. This impregnated layer was then dried in a convection oven at 50° C. for 10 minutes.

The second layer was then fixed at one edge to the first by a strip of double-faced adhesive tape.

Test Solution

Theophylline was added to aliquots of water to give final theophylline concentrations of 0.5, 1.0, 2.5, 5.0 and 40 µg/ml, respectively.

Analytical Procedure

The analytical elements which had been prepared and fixed to polystyrene supports as described above were each inserted into a mechanical holder suitable for horizontally positioning the device in a reflectance photometer. Just prior to inserting the element and holder into the photometer, a 50 µl aliquot of one of the theophylline solutions, prepared as described above, as pipetted onto the exposed surface. The photometer had been adjusted to follow changes in reflectance at 500 nm.

The reflectance of each was first measured over time (0–200 seconds) and then readings of each were taken at 200 seconds ($K/S = (1-R)^2/2R$, where R is reflectance).

Results

Figure 16:
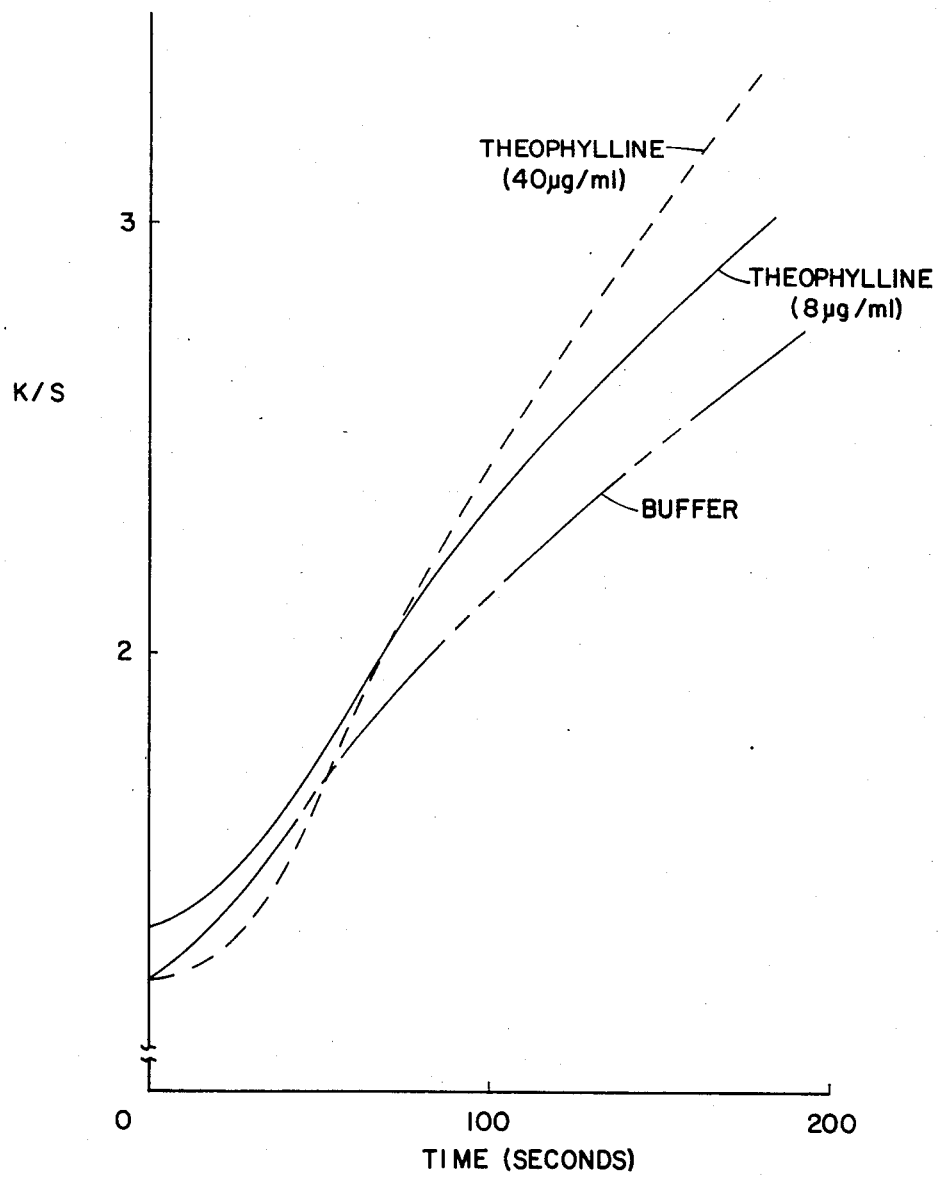

The data obtained by the above-described procedure is graphically illustrated in FIG. 16.

Conclusion

The resultant data shows the integral analytical element to provide a semi-quantitative detectable response to the theophylline concentration of each of the aliquots tested.

What is claimed is:

1. A test device for determining a ligand in a liquid sample based on competitive protein binding, the test device comprising
   (a) a first solid matrix layer element incorporated with an antibody or other naturally occurring binding protein for said ligand; and
   (b) a second solid matrix layer element incorporated with a labeled reagent comprising said ligand, or a binding analog thereof, chemically coupled with a label which is detectable by an electromagnetic signal that has a wavelength between about 200 and about 900 nanometers and is distinguishable when the labeled reagent is bound by the antibody or said other binding protein compared to when it is not so bound, the first and second layer elements each having a dry thickness of between about 5 and about 100 microns and being in laminar contact such that the liquid sample is capable of passing between superposed surfaces of such layer elements.

2. The device of claim 1 wherein said layer elements are web matrices comprised of natural or synthetic polymer fibers.

3. The device of claim 1 wherein said layer elements are polymeric films or gels.

4. The device of claim 1 wherein said label is a participant in an enzyme catalyzed reaction which produces said electromagnetic signal.

5. The device of claim 4 wherein said label is an enzyme substrate, a coenzyme, an enzyme modulator, or an enzyme.

6. The device of claim 1 wherein said ligand is selected from the group consisting of antigens and antibodies thereto; haptens and antibodies thereto; and hormones, vitamins, metabolites, and pharmacological agents, and their receptors and binding substances.

* * * * *